(12) United States Patent
Yamaoka

(10) Patent No.: US 7,803,592 B2
(45) Date of Patent: Sep. 28, 2010

(54) MUTANT GLUCOSE DEHYDROGENASE

(75) Inventor: Hideaki Yamaoka, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 754 days.

(21) Appl. No.: 11/587,333

(22) PCT Filed: Apr. 22, 2005

(86) PCT No.: PCT/JP2005/007687

§ 371 (c)(1),
(2), (4) Date: Oct. 19, 2006

(87) PCT Pub. No.: WO2005/103248

PCT Pub. Date: Nov. 3, 2005

(65) Prior Publication Data

US 2008/0280312 A1    Nov. 13, 2008

(30) Foreign Application Priority Data

Apr. 23, 2004 (JP) ............................. 2004-128165

(51) Int. Cl.
*C12N 9/04* (2006.01)
*C12N 1/20* (2006.01)
*C12N 15/00* (2006.01)
*C12Q 1/00* (2006.01)
*C12Q 1/68* (2006.01)
*C12Q 1/26* (2006.01)
*C12P 21/04* (2006.01)
*C07H 21/04* (2006.01)

(52) U.S. Cl. ............................. 435/190; 435/4; 435/6; 435/25; 435/440; 435/69.1; 435/71.1; 435/252.3; 435/320.1; 536/23.2

(58) Field of Classification Search .................. None
See application file for complete search history.

(56) References Cited

U.S. PATENT DOCUMENTS 6,103,509 A * 8/2000 Sode ........................ 435/190

FOREIGN PATENT DOCUMENTS

| EP | 1 176 202 | 1/2002 |
|---|---|---|
| EP | 1 331 272 | 7/2003 |
| EP | 1 367 120 | 12/2003 |
| EP | 1 498 484 | 1/2005 |
| EP | 1 535 997 | 6/2005 |
| EP | 1 536 014 | 6/2005 |
| JP | 2003 274964 | 9/2003 |
| WO | WO 2004/020638 | 3/2004 |
| WO | WO 2004/022732 | 3/2004 |

OTHER PUBLICATIONS

Yoshida et al. Engineering a chimeric pyrroloquinoline quinone glucose dehydrogenase: improvement of EDTA tolerance, thermal stability and substrate specificity. Protein Eng. Jan. 1999;12(1):63-70.*
Branden et al. Introduction to Protein Structure, Garland Publishing Inc., New York, p. 247, 1991.*
Sode et al. Biochem Biophys Res Commun. Jun. 6, 1995;211(1):268-7.*
Database UniProt Glucose Dehydrogenase from Burkholderia cepacia, Mar. 1, 2003, "Glucose Dehydrogenase," retrieved from EBI Database accession No. Q8GQE7 (abstract).
Inose, et al. "Cloning and Expression of the Gene Encoding Catalytic Subunit of Thermostable Glucose Dehydrogenase from *Burkholderia cepacia* in *Escherichia coli*," *Biochimica et Biophysics Acta*, vol. 1645, No. 2, pp. 133-138, Feb. 21, 2003.
Igarashi, et al. "Construction and Characterization of Mutant Water-Soluble PQQ Glucose Dehydrogenases with Altered $K_m$ Values—Site-Directed Mutagenesis Studies on the Putative Active Site," *Biochemical and Biophysical Research Communications*, vol. 264, pp. 820-824, Nov. 2, 1999.
Supplementary European Search Report dated Dec. 6, 2007.
Sode, et al. Improved Substrate Specificity and Dynamic Range for Glucose Measurement of *Escherichia coli* PQQ Glucose Dehydrogenase by Site Directed Mutagenesis, *Biotechnology Letters*, vol. 19, No. 11, pp. 1073-1077, Nov. 1997.
International Search Report dated July 22, 2005.

* cited by examiner

*Primary Examiner*—Yong D Pak
(74) *Attorney, Agent, or Firm*—Knobbe, Martens, Olson & Bear, LLP

(57) ABSTRACT

Substrate specificity for glucose of a glucose dehydrogenase having the amino acid sequence of SEQ ID NO: 13 is improved by substituting another amino acid residue for the amino acid residue at position 472 and/or 475.

14 Claims, 16 Drawing Sheets

Fig. 6

Primer: Wild Type (FW)

| 465 | 466 | 467 | 468 | 469 | 470 | 471 | 472 | 473 | 474 | 475 | 476 | 477 | 478 |
|---|---|---|---|---|---|---|---|---|---|---|---|---|---|
| C | GTG | TTC | AAC | GAC | GAA | TTC | GCG | CCG | AAC | AAC | CAC | ATC | AC |
|   | V | F | N | D | E | F | A | P | N | N | H | I |   |

5'- ... -3'

Primer: Wild type (RV)

| 478 | 477 | 476 | 475 | 474 | 473 | 472 | 471 | 470 | 469 | 468 | 467 | 466 | 465 |
|---|---|---|---|---|---|---|---|---|---|---|---|---|---|
| GT | GAT | GTG | GTT | GTT | CGG | CGC | GAA | TTC | GTC | GTT | GAA | CAC | G |
|   | I | H | N | N | P | A | F | E | D | N | F | V |   |

5'- ... -3'

Substitute codon table

| | | FW | RV |
|---|---|---|---|
| Ala | A | GCG | CGC |
| Arg | R | CGC | GCG |
| Asn | N | AAC | GTT |
| Asp | D | GAT | GTC |
| Cys | C | TGC | GCA |
| Glu | E | GAA | TTC |
| Gln | Q | CAG | CTG |
| Gly | G | GGC | GCC |
| His | H | CAC | GTG |
| Ile | I | ATC | GAT |
| Leu | L | CTG | CAG |
| Lys | K | AAA | TTT |
| Met | M | ATG | CAT |
| Phe | F | TTT | AAA |
| Pro | P | CCG | CGG |
| Ser | S | AGC | GCT |
| Thr | T | ACC | GGT |
| Trp | W | TGG | CCA |
| Tyr | Y | TAT | ATA |
| Val | V | GTG | CAC |

SEQUENCE LISTING

```
<160> NUMBER OF SEQ ID NOS: 59

<210> SEQ ID NO 1
<211> LENGTH: 5
<212> TYPE: PRT
<213> ORGANISM: Burkhorderia cepacia

<400> SEQUENCE: 1

Glu His Lys Phe Asn
1               5

<210> SEQ ID NO 2
<211> LENGTH: 5
<212> TYPE: PRT
<213> ORGANISM: Burkhorderia cepacia

<400> SEQUENCE: 2

Asp Lys Met Asp Phe
1               5

<210> SEQ ID NO 3
<211> LENGTH: 9
<212> TYPE: PRT
<213> ORGANISM: Burkhorderia cepacia

<400> SEQUENCE: 3

Asp Ala Ile Gly Ile Pro Arg Pro Glu
1               5

<210> SEQ ID NO 4
<211> LENGTH: 35
<212> TYPE: PRT
<213> ORGANISM: Burkhorderia cepacia
```

-continued

```
<400> SEQUENCE: 4

Glu Phe Ala Pro Asn Asn His Ile Thr Gly Ser Thr Ile Met Gly Ala
 1               5                  10                  15

Asp Ala Arg Asp Ser Val Val Asp Lys Asp Cys Arg Thr Phe Asp His
             20                  25                  30

Pro Asn Leu
         35

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 5
catgccatgg cacacaacga caacac                                        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 6
gtcgacgatc ttcttccagc cgaacatcac                                    30

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 7
cgcgccgaac gatcacatca cgggc                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 8
gcccgtgatg tgatcgttcg gcgcg                                         25

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 9
gaattcgcgc cgaacgaaca catcacgggc tcg                                33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: primer
```

<400> SEQUENCE: 10

```
cgagcccgtg atgtgttcgt tcggcgcgaa ttc                                   33
```

<210> SEQ ID NO 11
<211> LENGTH: 2467
<212> TYPE: DNA
<213> ORGANISM: Burkhorderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(2466)

<400> SEQUENCE: 11

```
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
tacatttcag gtccgcgccg attttttgaga aatatcaagc gtggttttcc cgaatccggt    240
gttcgagaga aggaaac atg cac aac gac aac act ccc cac tcg cgt cgc        290
                  Met His Asn Asp Asn Thr Pro His Ser Arg Arg
                  1               5                   10 cac ggc gac gca gcc gca tca ggc atc acg cgg cgt caa tgg ttg caa       338
His Gly Asp Ala Ala Ala Ser Gly Ile Thr Arg Arg Gln Trp Leu Gln
            15                  20                  25 ggc gcg ctg gcg ctg acc gca gcg ggc ctc acg ggt tcg ctg aca ttg       386
Gly Ala Leu Ala Leu Thr Ala Ala Gly Leu Thr Gly Ser Leu Thr Leu
        30                  35                  40 cgg gcg ctt gca gac aac ccc ggc act gcg ccg ctc gat acg ttc atg       434
Arg Ala Leu Ala Asp Asn Pro Gly Thr Ala Pro Leu Asp Thr Phe Met
    45                  50                  55 acg ctt tcc gaa tcg ctg acc ggc aag aaa ggg ctc agc cgc gtg atc       482
Thr Leu Ser Glu Ser Leu Thr Gly Lys Lys Gly Leu Ser Arg Val Ile
60                  65                  70                  75 ggc gag cgc ctg ctg cag gcg ctg cag aag ggc tcg ttc aag acg gcc       530
Gly Glu Arg Leu Leu Gln Ala Leu Gln Lys Gly Ser Phe Lys Thr Ala
                80                  85                  90 gac agc ctg ccg cag ctc gcc ggc gcg ctc gcg tcc ggt tcg ctg acg       578
Asp Ser Leu Pro Gln Leu Ala Gly Ala Leu Ala Ser Gly Ser Leu Thr
            95                  100                 105 cct gaa cag gaa tcg ctc gca ctg acg atc ctc gag gcc tgg tat ctc       626
Pro Glu Gln Glu Ser Leu Ala Leu Thr Ile Leu Glu Ala Trp Tyr Leu
        110                 115                 120 ggc atc gtc gac aac gtc gtg att acg tac gag gaa gca tta atg ttc       674
Gly Ile Val Asp Asn Val Val Ile Thr Tyr Glu Glu Ala Leu Met Phe
    125                 130                 135 ggc gtc gtg tcc gat acg ctc gtg atc cgt tcg tat tgc ccc aac aaa       722
Gly Val Val Ser Asp Thr Leu Val Ile Arg Ser Tyr Cys Pro Asn Lys
140                 145                 150                 155 ccc ggc ttc tgg gcc gac aaa ccg atc gag agg caa gcc tg atg gcc        769
Pro Gly Phe Trp Ala Asp Lys Pro Ile Glu Arg Gln Ala       Met Ala
                160                 165                 170 gat acc gat acg caa aag gcc gac gtc gtc gtc gtt gga tcg ggt gtc       817
Asp Thr Asp Thr Gln Lys Ala Asp Val Val Val Val Gly Ser Gly Val
            175                 180                 185 gcg ggc gcg atc gtc gcg cat cag ctc gcg atg gcg ggc aag gcg gtg       865
Ala Gly Ala Ile Val Ala His Gln Leu Ala Met Ala Gly Lys Ala Val
```

-continued

|  |  |  | 190 |  |  |  | 195 |  |  |  | 200 |  |  |  |  |
|---|---|---|---|---|---|---|---|---|---|---|---|---|---|---|---|
| atc | ctg | ctc | gaa | gcg | ggc | ccg | cgc | atg | ccg | cgc | tgg | gaa | atc | gtc | gag | 913 |
| Ile | Leu | Leu | Glu | Ala | Gly | Pro | Arg | Met | Pro | Arg | Trp | Glu | Ile | Val | Glu |  |
|  |  | 205 |  |  |  |  | 210 |  |  |  |  | 215 |  |  |  |  |

| cgc | ttc | cgc | aat | cag | ccc | gac | aag | atg | gac | ttc | atg | gcg | ccg | tac | ccg | 961 |
| Arg | Phe | Arg | Asn | Gln | Pro | Asp | Lys | Met | Asp | Phe | Met | Ala | Pro | Tyr | Pro |  |
| 220 |  |  |  |  | 225 |  |  |  |  | 230 |  |  |  |  |  |  |

| tcg | agc | ccc | tgg | gcg | ccg | cat | ccc | gag | tac | ggc | ccg | ccg | aac | gac | tac | 1009 |
| Ser | Ser | Pro | Trp | Ala | Pro | His | Pro | Glu | Tyr | Gly | Pro | Pro | Asn | Asp | Tyr |  |
| 235 |  |  |  |  | 240 |  |  |  |  | 245 |  |  |  |  | 250 |  |

| ctg | atc | ctg | aag | ggc | gag | cac | aag | ttc | aac | tcg | cag | tac | atc | cgc | gcg | 1057 |
| Leu | Ile | Leu | Lys | Gly | Glu | His | Lys | Phe | Asn | Ser | Gln | Tyr | Ile | Arg | Ala |  |
|  |  |  |  | 255 |  |  |  |  | 260 |  |  |  |  | 265 |  |  |

| gtg | ggc | ggc | acg | acg | tgg | cac | tgg | gcc | gcg | tcg | gcg | tgg | cgc | ttc | att | 1105 |
| Val | Gly | Gly | Thr | Thr | Trp | His | Trp | Ala | Ala | Ser | Ala | Trp | Arg | Phe | Ile |  |
|  |  |  | 270 |  |  |  |  | 275 |  |  |  |  | 280 |  |  |  |

| ccg | aac | gac | ttc | aag | atg | aag | agc | gtg | tac | ggc | gtc | ggc | cgc | gac | tgg | 1153 |
| Pro | Asn | Asp | Phe | Lys | Met | Lys | Ser | Val | Tyr | Gly | Val | Gly | Arg | Asp | Trp |  |
|  |  |  |  | 285 |  |  |  |  | 290 |  |  |  |  | 295 |  |  |

| ccg | atc | cag | tac | gac | gat | ctc | gag | ccg | tac | tat | cag | cgc | gcg | gag | gaa | 1201 |
| Pro | Ile | Gln | Tyr | Asp | Asp | Leu | Glu | Pro | Tyr | Tyr | Gln | Arg | Ala | Glu | Glu |  |
|  |  |  |  | 300 |  |  |  |  | 305 |  |  |  |  | 310 |  |  |

| gag | ctc | ggc | gtg | tgg | ggc | ccg | ggc | ccc | gag | gaa | gat | ctg | tac | tcg | ccg | 1249 |
| Glu | Leu | Gly | Val | Trp | Gly | Pro | Gly | Pro | Glu | Glu | Asp | Leu | Tyr | Ser | Pro |  |
| 315 |  |  |  |  | 320 |  |  |  |  | 325 |  |  |  |  | 330 |  |

| cgc | aag | cag | ccg | tat | ccg | atg | ccg | ccg | ctg | ccg | ttg | tcg | ttc | aac | gag | 1297 |
| Arg | Lys | Gln | Pro | Tyr | Pro | Met | Pro | Pro | Leu | Pro | Leu | Ser | Phe | Asn | Glu |  |
|  |  |  |  | 335 |  |  |  |  | 340 |  |  |  |  | 345 |  |  |

| cag | acc | atc | aag | acg | gcg | ctg | aac | aac | tac | gat | ccg | aag | ttc | cat | gtc | 1345 |
| Gln | Thr | Ile | Lys | Thr | Ala | Leu | Asn | Asn | Tyr | Asp | Pro | Lys | Phe | His | Val |  |
|  |  |  | 350 |  |  |  |  | 355 |  |  |  |  | 360 |  |  |  |

| gtg | acc | gag | ccg | gtc | gcg | cgc | aac | agc | cgc | ccg | tac | gac | ggc | cgc | ccg | 1393 |
| Val | Thr | Glu | Pro | Val | Ala | Arg | Asn | Ser | Arg | Pro | Tyr | Asp | Gly | Arg | Pro |  |
|  |  | 365 |  |  |  |  | 370 |  |  |  |  | 375 |  |  |  |  |

| act | tgt | tgc | ggc | aac | aac | aac | tgc | atg | ccg | atc | tgc | ccg | atc | ggc | gcg | 1441 |
| Thr | Cys | Cys | Gly | Asn | Asn | Asn | Cys | Met | Pro | Ile | Cys | Pro | Ile | Gly | Ala |  |
| 380 |  |  |  |  | 385 |  |  |  |  | 390 |  |  |  |  |  |  |

| atg | tac | aac | ggc | atc | gtg | cac | gtc | gag | aag | gcc | gaa | cgc | gcc | ggc | gcg | 1489 |
| Met | Tyr | Asn | Gly | Ile | Val | His | Val | Glu | Lys | Ala | Glu | Arg | Ala | Gly | Ala |  |
| 395 |  |  |  |  | 400 |  |  |  |  | 405 |  |  |  |  | 410 |  |

| aag | ctg | atc | gag | aac | gcg | gtc | gtc | tac | aag | ctc | gag | acg | ggc | ccg | gac | 1537 |
| Lys | Leu | Ile | Glu | Asn | Ala | Val | Val | Tyr | Lys | Leu | Glu | Thr | Gly | Pro | Asp |  |
|  |  |  |  | 415 |  |  |  |  | 420 |  |  |  |  | 425 |  |  |

| aag | cgc | atc | gtc | gcg | gcg | ctc | tac | aag | gac | aag | acg | ggc | gcc | gag | cat | 1585 |
| Lys | Arg | Ile | Val | Ala | Ala | Leu | Tyr | Lys | Asp | Lys | Thr | Gly | Ala | Glu | His |  |
|  |  |  | 430 |  |  |  |  | 435 |  |  |  |  | 440 |  |  |  |

| cgc | gtc | gaa | ggc | aag | tat | ttc | gtg | ctc | gcc | gcg | aac | ggc | atc | gag | acg | 1633 |
| Arg | Val | Glu | Gly | Lys | Tyr | Phe | Val | Leu | Ala | Ala | Asn | Gly | Ile | Glu | Thr |  |
|  |  | 445 |  |  |  |  | 450 |  |  |  |  | 455 |  |  |  |  |

| ccg | aag | atc | ctg | ctg | atg | tcc | gcg | aac | cgc | gat | ttc | ccg | aac | ggt | gtc | 1681 |
| Pro | Lys | Ile | Leu | Leu | Met | Ser | Ala | Asn | Arg | Asp | Phe | Pro | Asn | Gly | Val |  |
|  | 460 |  |  |  |  | 465 |  |  |  |  | 470 |  |  |  |  |  |

| gcg | aac | agc | tcg | gac | atg | gtc | ggc | cgc | aac | ctg | atg | gac | cat | ccg | ggc | 1729 |
| Ala | Asn | Ser | Ser | Asp | Met | Val | Gly | Arg | Asn | Leu | Met | Asp | His | Pro | Gly |  |
| 475 |  |  |  |  | 480 |  |  |  |  | 485 |  |  |  |  | 490 |  |

| acc | ggc | gtg | tcg | ttc | tat | gcg | agc | gag | aag | ctg | tgg | ccg | ggc | cgc | ggc | 1777 |
| Thr | Gly | Val | Ser | Phe | Tyr | Ala | Ser | Glu | Lys | Leu | Trp | Pro | Gly | Arg | Gly |  |
|  |  |  |  | 495 |  |  |  |  | 500 |  |  |  |  | 505 |  |  |

| ccg | cag | gag | atg | acg | tcg | ctg | atc | ggt | ttc | cgc | gac | ggt | ccg | ttc | cgc | 1825 |

```
Pro Gln Glu Met Thr Ser Leu Ile Gly Phe Arg Asp Gly Pro Phe Arg
            510                 515                 520 gcg acc gaa gcg gcg aag aag atc cac ctg tcg aac ctg tcg cgc atc         1873
Ala Thr Glu Ala Ala Lys Lys Ile His Leu Ser Asn Leu Ser Arg Ile
            525                 530                 535 gac cag gag acg cag aag atc ttc aag gcc ggc aag ctg atg aag ccc         1921
Asp Gln Glu Thr Gln Lys Ile Phe Lys Ala Gly Lys Leu Met Lys Pro
540                 545                 550 gac gag ctc gac gcg cag atc cgc gac cgt tcc gca cgc tac gtg cag         1969
Asp Glu Leu Asp Ala Gln Ile Arg Asp Arg Ser Ala Arg Tyr Val Gln
555                 560                 565                 570 ttc gac tgc ttc cac gaa atc ctg ccg caa ccc gag aac cgc atc gtg         2017
Phe Asp Cys Phe His Glu Ile Leu Pro Gln Pro Glu Asn Arg Ile Val
            575                 580                 585 ccg agc aag acg gcg acc gat gcg atc ggc att ccg cgc ccc gag atc         2065
Pro Ser Lys Thr Ala Thr Asp Ala Ile Gly Ile Pro Arg Pro Glu Ile
            590                 595                 600 acg tat gcg atc gac gac tac gtg aag cgc ggc gcc gcg cat acg cgc         2113
Thr Tyr Ala Ile Asp Asp Tyr Val Lys Arg Gly Ala Ala His Thr Arg
            605                 610                 615 gag gtc tac gcg acc gcc gcg aag gtg ctc ggc ggc acg gac gtc gtg         2161
Glu Val Tyr Ala Thr Ala Ala Lys Val Leu Gly Gly Thr Asp Val Val
620                 625                 630 ttc aac gac gaa ttc gcg ccg aac aat cac atc acg ggc tcg acg atc         2209
Phe Asn Asp Glu Phe Ala Pro Asn Asn His Ile Thr Gly Ser Thr Ile
635                 640                 645                 650 atg ggc gcc gat gcg cgc gac tcc gtc gtc gac aag gac tgc cgc acg         2257
Met Gly Ala Asp Ala Arg Asp Ser Val Val Asp Lys Asp Cys Arg Thr
            655                 660                 665 ttc gac cat ccg aac ctg ttc att tcg agc agc gcg acg atg ccg acc         2305
Phe Asp His Pro Asn Leu Phe Ile Ser Ser Ser Ala Thr Met Pro Thr
            670                 675                 680 gtc ggt acc gta aac gtg acg ctg acg atc gcc gcg ctc gcg ctg cgg         2353
Val Gly Thr Val Asn Val Thr Leu Thr Ile Ala Ala Leu Ala Leu Arg
            685                 690                 695 atg tcg gac acg ctg aag aag gaa gtc tgacc gtg cgg aaa tct act ctc      2403
Met Ser Asp Thr Leu Lys Lys Glu Val       Val Arg Lys Ser Thr Leu
700                 705                           710 act ttc ctc atc gcc ggc tgc ctc gcg ttg ccg ggc ttc gcg cgc gcg         2451
Thr Phe Leu Ile Ala Gly Cys Leu Ala Leu Pro Gly Phe Ala Arg Ala
            715                 720                 725 gcc gat gcg gcc gat c                                                    2467
Ala Asp Ala Ala Asp
730

<210> SEQ ID NO 12
<211> LENGTH: 168
<212> TYPE: PRT
<213> ORGANISM: Burkhorderia cepacia

<400> SEQUENCE: 12

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
                20                  25                  30

Thr Ala Ala Gly Leu Thr Gly Ser Leu Thr Leu Arg Ala Leu Ala Asp
            35                  40                  45

Asn Pro Gly Thr Ala Pro Leu Asp Thr Phe Met Thr Leu Ser Glu Ser
        50                  55                  60
```

-continued

```
Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 13
<211> LENGTH: 539
<212> TYPE: PRT
<213> ORGANISM: Burkhorderia cepacia

<400> SEQUENCE: 13

Met Ala Asp Thr Asp Thr Gln Lys Ala Asp Val Val Val Val Gly Ser
 1               5                  10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270
```

-continued

```
Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 14
<211> LENGTH: 27
<212> TYPE: PRT
<213> ORGANISM: Burkhorderia cepacia

<400> SEQUENCE: 14

Val Arg Lys Ser Thr Leu Thr Phe Leu Ile Ala Gly Cys Leu Ala Leu
 1               5                  10                  15

Pro Gly Phe Ala Arg Ala Ala Asp Ala Ala Asp
            20                  25

<210> SEQ ID NO 15
<211> LENGTH: 1441
<212> TYPE: DNA
<213> ORGANISM: Burkholderia cepacia
<220> FEATURE:
<221> NAME/KEY: CDS
<222> LOCATION: (121)..(1398)

<400> SEQUENCE: 15
tccgaacctg ttcatttcga gcagcgcgac gatgccgacc gtcggtaccg taaacgtgac      60
```

-continued

```
gctgacgatc gccgcgctcg cgctgcggat gtcggacacg ctgaagaagg aagtctgacc    120 gtg cgg aaa tct act ctc act ttc ctc atc gcc ggc tgc ctc gcg ttg    168
Val Arg Lys Ser Thr Leu Thr Phe Leu Ile Ala Gly Cys Leu Ala Leu
 1               5                   10                  15 ccg ggc ttc gcg cgc gcg gcc gat gcg gcc gat ccg gcg ctg gtc aag    216
Pro Gly Phe Ala Arg Ala Ala Asp Ala Ala Asp Pro Ala Leu Val Lys
             20                  25                  30 cgc ggc gaa tac ctc gcg acc gcc atg ccg gta ccg atg ctc ggc aag    264
Arg Gly Glu Tyr Leu Ala Thr Ala Met Pro Val Pro Met Leu Gly Lys
         35                  40                  45 atc tac acg agc aac atc acg ccc gat ccc gat acg ggc gac tgc atg    312
Ile Tyr Thr Ser Asn Ile Thr Pro Asp Pro Asp Thr Gly Asp Cys Met
     50                  55                  60 gcc tgc cac acc gtg aag ggc ggc aag ccg tac gcg ggc ggc ctt ggc    360
Ala Cys His Thr Val Lys Gly Gly Lys Pro Tyr Ala Gly Gly Leu Gly
 65                  70                  75                  80 ggc atc ggc aaa tgg acg ttc gag gac ttc gag cgc gcg gtg cgg cac    408
Gly Ile Gly Lys Trp Thr Phe Glu Asp Phe Glu Arg Ala Val Arg His
             85                  90                  95 ggc gtg tcg aag aac ggc gac aac ctg tat ccg gcg atg ccg tac gtg    456
Gly Val Ser Lys Asn Gly Asp Asn Leu Tyr Pro Ala Met Pro Tyr Val
        100                 105                 110 tcg tac gcg aag atc aag gac gac gac gta cgc gcg ctg tac gcc tac    504
Ser Tyr Ala Lys Ile Lys Asp Asp Asp Val Arg Ala Leu Tyr Ala Tyr
        115                 120                 125 ttc atg cac ggc gtc gag ccg gtc aag cag gcg ccg ccg aag aac gag    552
Phe Met His Gly Val Glu Pro Val Lys Gln Ala Pro Pro Lys Asn Glu
        130                 135                 140 atc cca gcg ctg cta agc atg cgc tgg ccg ctg aag atc tgg aac tgg    600
Ile Pro Ala Leu Leu Ser Met Arg Trp Pro Leu Lys Ile Trp Asn Trp
145                 150                 155                 160 ctg ttc ctg aag gac ggc ccg tac cag ccg aag ccg tcg cag agc gcc    648
Leu Phe Leu Lys Asp Gly Pro Tyr Gln Pro Lys Pro Ser Gln Ser Ala
                165                 170                 175 gaa tgg aat cgc ggc gcg tat ctg gtg cag ggt ctc gcg cac tgc agc    696
Glu Trp Asn Arg Gly Ala Tyr Leu Val Gln Gly Leu Ala His Cys Ser
            180                 185                 190 acg tgc cac acg ccg cgc ggc atc gcg atg cag gag aag tcg ctc gac    744
Thr Cys His Thr Pro Arg Gly Ile Ala Met Gln Glu Lys Ser Leu Asp
        195                 200                 205 gaa acc ggc ggc agc ttc ctc gcg ggg tcg gtg ctc gcc ggc tgg gac    792
Glu Thr Gly Gly Ser Phe Leu Ala Gly Ser Val Leu Ala Gly Trp Asp
        210                 215                 220 ggc tac aac atc acg tcg gac ccg aat gcg ggg atc ggc agc tgg acg    840
Gly Tyr Asn Ile Thr Ser Asp Pro Asn Ala Gly Ile Gly Ser Trp Thr
225                 230                 235                 240 cag cag cag ctc gtg cag tat ttg cgc acc ggc agc gtg ccg ggc gtc    888
Gln Gln Gln Leu Val Gln Tyr Leu Arg Thr Gly Ser Val Pro Gly Val
                245                 250                 255 gcg cag gcg gcc ggg ccg atg gcc gag gcg gtc gag cac agc ttc tcg    936
Ala Gln Ala Ala Gly Pro Met Ala Glu Ala Val Glu His Ser Phe Ser
            260                 265                 270 aag atg acc gaa gcg gac atc ggt gcg atc gcc acg tac gtc cgc acg    984
Lys Met Thr Glu Ala Asp Ile Gly Ala Ile Ala Thr Tyr Val Arg Thr
        275                 280                 285 gtg ccg gcc gtt gcc gac agc aac gcg aag cag ccg cgg tcg tcg tgg   1032
Val Pro Ala Val Ala Asp Ser Asn Ala Lys Gln Pro Arg Ser Ser Trp
        290                 295                 300 ggc aag ccg gcc gag gac ggg ctg aag ctg cgc ggt gtc gcg ctc gcg   1080
Gly Lys Pro Ala Glu Asp Gly Leu Lys Leu Arg Gly Val Ala Leu Ala
```

```
Gly Lys Pro Ala Glu Asp Gly Leu Lys Leu Arg Gly Val Ala Leu Ala
305                 310                 315                 320 tcg tcg ggc atc gat ccg gcg cgg ctg tat ctc ggc aac tgc gcg acg    1128
Ser Ser Gly Ile Asp Pro Ala Arg Leu Tyr Leu Gly Asn Cys Ala Thr
                325                 330                 335 tgc cac cag atg cag ggc aag ggc acg ccg gac ggt tac tac ccg tcg    1176
Cys His Gln Met Gln Gly Lys Gly Thr Pro Asp Gly Tyr Tyr Pro Ser
            340                 345                 350 ctg ttc cac aac tcc acc gtc ggc gcg tcg aat ccg tcg aac ctc gtg    1224
Leu Phe His Asn Ser Thr Val Gly Ala Ser Asn Pro Ser Asn Leu Val
        355                 360                 365 cag gtg atc ctg aac ggc gtg cag cgc aag atc ggc agc gag gat atc    1272
Gln Val Ile Leu Asn Gly Val Gln Arg Lys Ile Gly Ser Glu Asp Ile
    370                 375                 380 ggg atg ccc gct ttc cgc tac gat ctg aac gac gcg cag atc gcc gcg    1320
Gly Met Pro Ala Phe Arg Tyr Asp Leu Asn Asp Ala Gln Ile Ala Ala
385                 390                 395                 400 ctg acg aac tac gtg acc gcg cag ttc ggc aat ccg gcg gcg aag gtg    1368
Leu Thr Asn Tyr Val Thr Ala Gln Phe Gly Asn Pro Ala Ala Lys Val
                405                 410                 415 acg gag cag gac gtc gcg aag ctg cgc tga catagtcggg cgcgccgaca      1418
Thr Glu Gln Asp Val Ala Lys Leu Arg
            420                 425 cggcgcaacc gataggacag gag                                          1441

<210> SEQ ID NO 16
<211> LENGTH: 425
<212> TYPE: PRT
<213> ORGANISM: Burkholderia cepacia

<400> SEQUENCE: 16

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
                20                  25                  30

Arg Gly Glu Tyr Leu Ala Thr Ala Met Pro Val Pro Met Leu Gly Lys
            35                  40                  45

Ile Tyr Thr Ser Asn Ile Thr Pro Asp Pro Thr Gly Asp Cys Met
        50                  55                  60

Ala Cys His Thr Val Lys Gly Gly Lys Pro Tyr Ala Gly Gly Leu Gly
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Lys Asp Asp Val Arg Ala Leu Tyr Ala Tyr
        115                 120                 125

Phe Met His Gly Val Glu Pro Val Lys Gln Ala Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205
```

```
Glu Thr Gly Gly Ser Phe Leu Ala Gly Ser Val Leu Ala Gly Trp Asp
    210                 215                 220
Gly Tyr Asn Ile Thr Ser Asp Pro Asn Ala Gly Ile Gly Ser Trp Thr
225                 230                 235                 240
Gln Gln Gln Leu Val Gln Tyr Leu Arg Thr Gly Ser Val Pro Gly Val
                245                 250                 255
Ala Gln Ala Ala Gly Pro Met Ala Glu Ala Val Glu His Ser Phe Ser
            260                 265                 270
Lys Met Thr Glu Ala Asp Ile Gly Ala Ile Ala Thr Tyr Val Arg Thr
        275                 280                 285
Val Pro Ala Val Ala Asp Ser Asn Ala Lys Gln Pro Arg Ser Ser Trp
    290                 295                 300
Gly Lys Pro Ala Glu Asp Gly Leu Lys Leu Arg Gly Val Ala Leu Ala
305                 310                 315                 320
Ser Ser Gly Ile Asp Pro Ala Arg Leu Tyr Leu Gly Asn Cys Ala Thr
                325                 330                 335
Cys His Gln Met Gln Gly Lys Gly Thr Pro Asp Gly Tyr Tyr Pro Ser
            340                 345                 350
Leu Phe His Asn Ser Thr Val Gly Ala Ser Asn Pro Ser Asn Leu Val
        355                 360                 365
Gln Val Ile Leu Asn Gly Val Gly Arg Lys Ile Gly Ser Glu Asp Ile
    370                 375                 380
Gly Met Pro Ala Phe Arg Tyr Asp Leu Asn Asp Ala Gln Ile Ala Ala
385                 390                 395                 400
Leu Thr Asn Tyr Val Thr Ala Gln Phe Gly Asn Pro Ala Ala Lys Val
                405                 410                 415
Thr Glu Gln Asp Val Ala Lys Leu Arg
            420                 425
```

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 17
cctgttcaac gacgaattcg cgccgaacaa ccacatcac                    39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 18
gtgatgtggt tgttcggcgc gaattcgtcg ttgaacacg                    39

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 19
cgatccgaac catcacttta cgggctcgac gatca                        35

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 20
cgatccgaac catcacatct ttggctcgac gatcatggg                    39

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 21
tccgaaccat cacatcacgt tttcgacgat catgggcgc                    39

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 22
catcacatca cgggctttac gatcatgggc gcc                          33

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 23
atcacatcac gggctcgttt atcatgggcg ccgatgc                      37

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 24
cacgggctcg acgtttatgg gcgccgatg                               29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 25
cgggctcgac gatctttggc gccgatgcg                               29

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: primer -continued

```
<400> SEQUENCE: 26
gggctcgacg atcatgtttg ccgatgcgcg cga                                    33

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 27
gctcgacgat catgggcttt gatgcgcgcg actcc                                  35

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 28
cgatcatggg cgcctttgcg cgcgactcc                                         29

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 29
cgatcatggg cgccgatttt cgcgactccg tcgtc                                  35

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 30
tgggcgccga tgcgtttgac tccgtcgtcg aca                                    33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 31
gcgccgatgc gcgctttcc gtcgtcgaca agg                                     33

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 32
cgatgcgcgc gactttgtcg tcgacaagga c                                      31

<210> SEQ ID NO 33
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 33
tgcgcgcgac tcctttgtcg acaaggactg c                                      31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 34
cgcgcgactc cgtctttgac aaggactgcc g                                      31

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 35
cgcgactccg tcgtctttaa ggactgccgc acg                                    33

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 36
cgactccgtc gtcgactttg actgccgcac gttcg                                  35

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 37
ctccgtcgtc gacaagtttt gccgcacgtt cgacc                                  35

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 38
cgtcgtcgac aaggactttc gcacgttcga ccatc                                  35

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 39
gtcgtcgaca aggactgctt tacgttcgac catccgaac                           39

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 40
ggaaatcgtc gagcgcttct ttaatcagcc cgacaagatg g                        41

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 41
cgagcgcttc cgctttcagc ccgacaagat g                                   31

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 42
gtcgagcgct tccgcaattt tcccgacaag atggacttc                           39

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 43
gagcgcttcc gcaatcagtt tgacaagatg gacttcatgg c                        41

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 44
gcttccgcaa tcagcccttt aagatggact tcatggcgc                           39

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 45
ccgcaatcag cccgacttta tggacttcat ggcgccg                             37

<210> SEQ ID NO 46
<211> LENGTH: 35
<212> TYPE: DNA

-continued

```
<213> ORGANISM: Artificial Sequence
<220> FEATURE:
<223> OTHER INFORMATION: Description of Artificial Sequence: primer

<400> SEQUENCE: 46
gcaatcagcc cgacaagttt gacttcatgg cgccg                          35

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 47
caatcagccc gacaagatgt ttttcatggc gccgtaccc                      39

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 48
cgacaagatg gacttctttg cgccgtaccc gtc                            33

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 49
cgacaagatg gacttcatgt ttccgtaccc gtcgagccc                      39

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 50
caagatggac ttcatggcgt tttacccgtc gagcccctg                      39

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 51
acttcatggc gccgtttccg tcgagcccc                                 29

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 52
cttcatggcg ccgtactttt cgagcccctg ggc                            33
```

-continued

```
<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 53
gcgccgtacc cgtttagccc ctgggcg                                           27

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 54
cgccgtaccc gtcgtttccc tgggcgccg                                         29

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 55
ccgtacccgt cgagcttttg ggcgccgcat ccc                                    33

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 56
ccgtcgagcc cctttgcgcc gcatccc                                           27

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 57
cgtcgagccc ctggtttccg catcccgagt acg                                    33

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 58
cgagcccctg ggcgtttcat cccgagtacg gcc                                    33

<210> SEQ ID NO 59
<211> LENGTH: 27
<212> TYPE: DNA
<213> ORGANISM: Artificial Sequence
<220> FEATURE:
```

-continued

```
<223> OTHER INFORMATION: Description of Artificial Sequence: primer

<400> SEQUENCE: 59
ccctgggcgc cgtttcccga gtacggc                                              27
```

MUTANT GLUCOSE DEHYDROGENASE

RELATED APPLICATIONS

This is the U.S. National Phase under 35 U.S.C. §371 of International Application PCT/JP2005/007687, filed Apr. 22, 2005, which was published in a language other than English, which claims priority of JP Application No. 2004-128165, filed Apr. 23, 2004.

TECHNICAL FIELD

The present invention relates to a mutant glucose dehydrogenase showing improved substrate specificity. The mutant glucose dehydrogenase of the present invention can be suitably used for glucose sensors, glucose assay kits and so forth, and is useful in the fields of biochemistry, clinical medicine, and so forth.

BACKGROUND ART

In recent years, a variety of enzymes are used as biosensor elements. Glucose oxidases (GODs) have already been practically used as sensor elements for measuring blood glucose levels for the purpose of diagnosis of diabetes. However, GODs suffer from a problem that they are affected by dissolved oxygen in samples. Therefore, glucose dehydrogenases (GDHs), which are not affected by dissolved oxygen in samples, are drawing attentions as alternatives of GODs.

As GDHs, one requiring $NAD(P)^+$ as a coenzyme (E.C.1.1.1.47), one requiring pyroloquinoline quinone (PQQ) as a coenzyme (PQQGDH; E.C.1.1.99.17) etc. have been reported. GDH requiring $NAD(P)^+$ as a coenzyme suffers from a problem as a sensor element that $NAD(P)^+$ needs to be added to the assay system. On the other hand, it is unnecessary for coenzyme-binding type GDHs such as PQQGDH to add a coenzyme to the assay system.

Further, sensor elements are desired to exhibit a stability that the function as a sensor is not lost even when they are continuously used or left at room temperature.

Since enzymes derived from thermophilic bacteria which grow at high temperature generally exhibit high thermostability, and high stability even in long-term storage, continuous use and so forth, application of them as sensor elements is expected. However, although GDHs derived from *Thermoplasma acidophilum* and *Sulfolobus solfataricus* have been reported as thermostable GDHs derived from thermophilic bacteria, both of them require $NAD(P)^+$ as a coenzyme.

On the other hand, thermostable GDH produced by *Burkholderia cepacia*, a moderately thermophilic bacterium, is an FAD-binding type GDH, and the enzymological characteristics thereof such as optimum reaction temperature, thermostability and substrate specificity have already been elucidated (Patent document 1). This GDH usually exists as a heterooligomer consisting of a catalytic subunit (α-subunit) showing high heat resistance, an electron transfer subunit (β-subunit), which is cytochrome C, and γ-subunit of which function is unknown, and its optimum reaction temperature is 45° C. These subunits are dissociated by a heat treatment at a temperature higher than 50° C. to release the α-subunit monomer of which optimum reaction temperature is 75° C. The α-subunit monomer is thermostable and exhibits 80% or more of residual activity even after a heat treatment at 60° C. for 30 minutes. The genes coding for these subunits have also already been isolated (Patent documents 1 and 2).

However, coenzyme-binding type GDHs generally exhibit a broad substrate specificity, and also react with maltose, galactose and so forth in addition to glucose. When they are applied as a glucose sensor for monitoring blood sugar levels of diabetic patients, and the diabetic patients have such severe symptoms that peritoneal dialysis must be performed, there is a risk that values higher than the true blood sugar levels may be obtained, because a large amount of maltose is contained in the dialysate. GDH derived from *Burkholderia cepacia* also exhibits reactivity to maltose and galactose in addition to glucose.

A technique of changing substrate specificity of GDH by introducing an amino acid substitution mutation is known. As such mutant GDHs, for example, there are known PQQGDHs derived from *E. coli* (Patent documents 3 and 4), *Acinetobacter calcoaceticus* (*Gluconobacter calcoaceticus*) (Patent document 5), and *Acinetobacter baumannii* (Patent documents 6 to 8) requiring pyroloquinoline quinone as a coenzyme.

[Patent document 1] U.S. Patent Application No. 2004/0023330
[Patent document 2] International Patent Publication WO03/091430
[Patent document 3] Japanese Patent Laid-open (Kokai) No. 10-243786
[Patent document 4] Japanese Patent Laid-open No. 2001-197888
[Patent document 5] Japanese Patent Laid-open No. 2004-173538
[Patent document 6] Japanese Patent Laid-open No. 2004-313172
[Patent document 7] Japanese Patent Laid-open No. 2004-313180
[Patent document 8] Japanese Patent Laid-open No. 2004-344145

DISCLOSURE OF THE INVENTION

An object of the present invention is to provide an FAD-binding type GDH showing an improved substrate specificity to glucose.

The inventors of the present invention conducted various researches in order to achieve the foregoing object. As a result, they found that by modifying the amino acid sequence of the FAD-binding type GDH derived from *Burkholderia cepacia* at a specific site, the reactivity thereof to sugars other than glucose could be decreased while maintaining the reactivity to glucose, and thus accomplished the present invention.

That is, the present invention provides the followings.
(1) A mutant glucose dehydrogenase exhibiting improved substrate specificity to glucose, which is a protein having the amino acid sequence of SEQ ID NO: 13 or an amino acid sequence of SEQ ID NO: 13 including substitution, deletion, insertion or addition of one or more amino acid residues at position other than the positions listed below and having a glucose dehydrogenase activity, and has any of the amino acid substitution mutations listed below (numerals represent a position in the amino acid sequence, the amino acid residues represent an amino acid residue after substitution at the position, and "+" means that two amino acid substitutions are simultaneously included):
(A) 472Arg, 472Asn, 472Asp, 472Cys, 472Glu, 472Gly, 472H is, 472Ile, 472Leu, 472Met, 472Phe, 472Pro, 472Ser, 472Trp, 472Tyr, 472Val,
(B) 475Asp, 475Cys, 475Glu, 475Gly, 475H is, 475Met, 475Phe, 475Ser, 475Tyr, 475Val,
(C) 472Arg+475(Asp, Glu, Gly, H is, Phe, Ser, Tyr), 472Asn+475(Asp, Gly, H is, Phe, Ser, Tyr), 472Asp+475(H is, Phe, Ser, Val), 472Cys+475(Asp, Gly, His, Phe, Ser), 472Glu+ 475(Asp, Glu, Gly, His, Phe, Ser, Tyr), 472Gly+475(Asp, Cys, Gly, Met, Phe, Ser, Tyr), 472His+475(Cys, Glu, His, Met, Phe, Ser, Tyr), 472Ile+475(Asp, Cys, Glu, Gly, His, Met, Phe, Ser, Tyr), 472Leu+475(Asp, Gly, His, Phe, Ser, Tyr), 472Met+475(Asp, Gly, His, Phe, Ser), 472Phe+475 (Asp, Glu, Gly, His, Met, Phe, Ser, Tyr), 472Pro+475His 472Ser+475(Asp, Glu, Gly, His, Phe, Ser), 472Trp+475(His, Phe, Ser), 472Tyr+475(Asp, His, Phe, Ser), 472Val+475 (Asp, Glu, Gly, His, Phe, Ser).

(2) The aforementioned mutant glucose dehydrogenase, which has the amino acid sequence of SEQ ID NO: 13 provided that it includes any of the amino acid substitution mutations listed in the aforementioned (A) to (C).

(3) The aforementioned mutant glucose dehydrogenase, which has an amino acid substitution mutation selected from the following mutations:

(D) 472Arg, 472Asn, 472Asp, 472Glu, 472Gly, 472Phe, 472Pro, (E) 475Asp, 475Cys, 475Glu, 475Gly, 475Met, 475Phe (F) 472Arg+475(Asp, Gly, His, Phe), 472Asn+475(Gly, His, Phe, Tyr), 472Asp+475(His, Ser), 472Cys+475(Gly, His, Phe), 472Glu+475(Glu, His, Phe, Tyr), 472Gly+475(Asp, Phe, Tyr), 472His+475(His, Ser), 472Ile+475(Asp, Glu, Gly, His, Ser), 472Leu+475(Gly, His, Phe, Tyr), 472Met+ 475(Asp, Gly, His, Phe), 472Phe+475(Asp, Glu, Gly, His, Phe, Ser, Tyr), 472Ser+475(Glu, Gly, His, Phe), 472Trp+ 475(His, Phe), 472Tyr+475His, 472Val+475(Asp, Glu, Gly, His, Phe).

(4) A glucose dehydrogenase, which is a protein having the amino acid sequence of SEQ ID NO: 13 or an amino acid sequence of SEQ ID NO: 13 including substitution, deletion, insertion or addition of one or more amino acid residues at position other than the positions listed below and having a glucose dehydrogenase activity, and wherein:

(i) at least either the arginine residue at position 472 or the asparagine residue at position 475 in the amino acid sequence of SEQ ID NO: 13 is replaced with another amino acid residue, and (ii) a ratio of specific activity for glucose and specific activity for maltose ((reactivity to maltose/reactivity to glucose)× 100) of the glucose dehydrogenase introduced with the aforementioned mutation is reduced by 10% or more compared with that of a glucose dehydrogenase not introduced with the mutation.

(5) A mutant glucose dehydrogenase complex comprising at least the aforementioned mutant glucose dehydrogenase and an electron transfer subunit.

(6) A DNA coding for the aforementioned mutant glucose dehydrogenase.

(7) A microorganism having the aforementioned DNA and producing the aforementioned mutant glucose dehydrogenase or the mutant glucose dehydrogenase complex.

(8) A glucose assay kit comprising the aforementioned mutant glucose dehydrogenase, the mutant glucose dehydrogenase complex, or the microorganism.

(9) A glucose sensor comprising the aforementioned mutant glucose dehydrogenase, the mutant glucose dehydrogenase complex, or the microorganism.

In the present specification, although the term "mutant GDH" refers to a mutant α-subunit in the context of contrast with a mutant GDH complex, a mutant α-subunit and a mutant GDH complex may also be collectively referred to as "mutant GDH".

BRIEF DESCRIPTION OF THE DRAWINGS

FIG. 6 shows sequences of PCR primers used for codon substitutions at positions 472 and 475 in the GDH α-subunit.

BEST MODE FOR CARRYING OUT THE INVENTION

Figure 1:
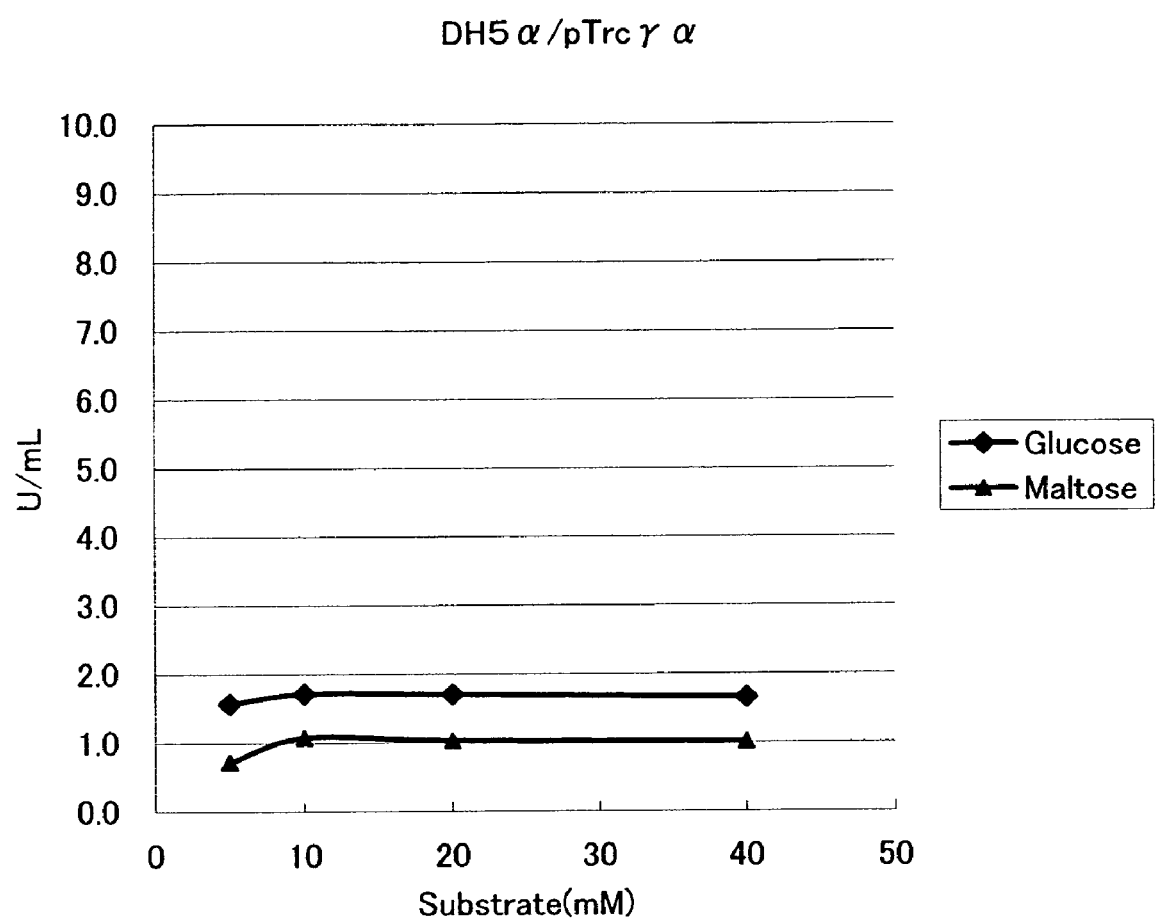
FIG. 1 shows dehydrogenase activities of DH5α/pTrc99A/γ+α for glucose and maltose as substrates. The rhombuses represent the activity for glucose, and the squares represents the activity for maltose (the same shall apply in FIGS. 2 to 5).
Figure 2:
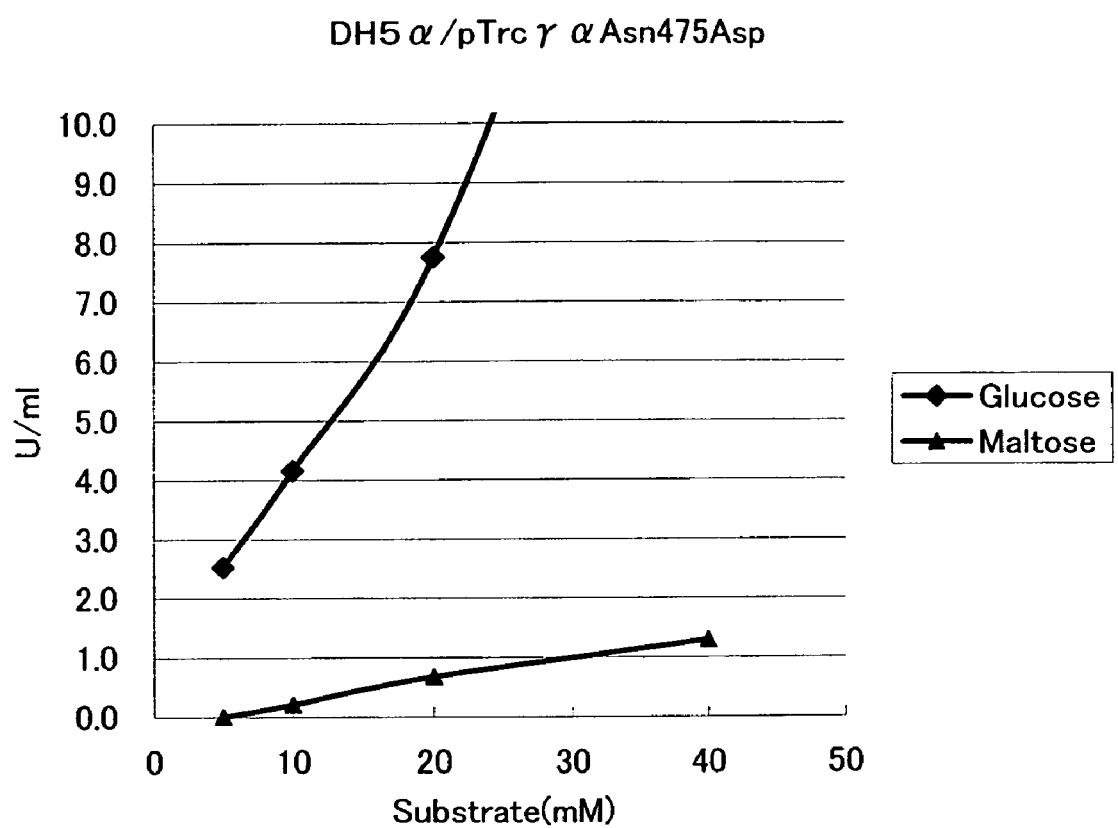
FIG. 2 shows dehydrogenase activities of DH5α/pTrcγαAsn475Asp for glucose and maltose as substrates.
Figure 3:
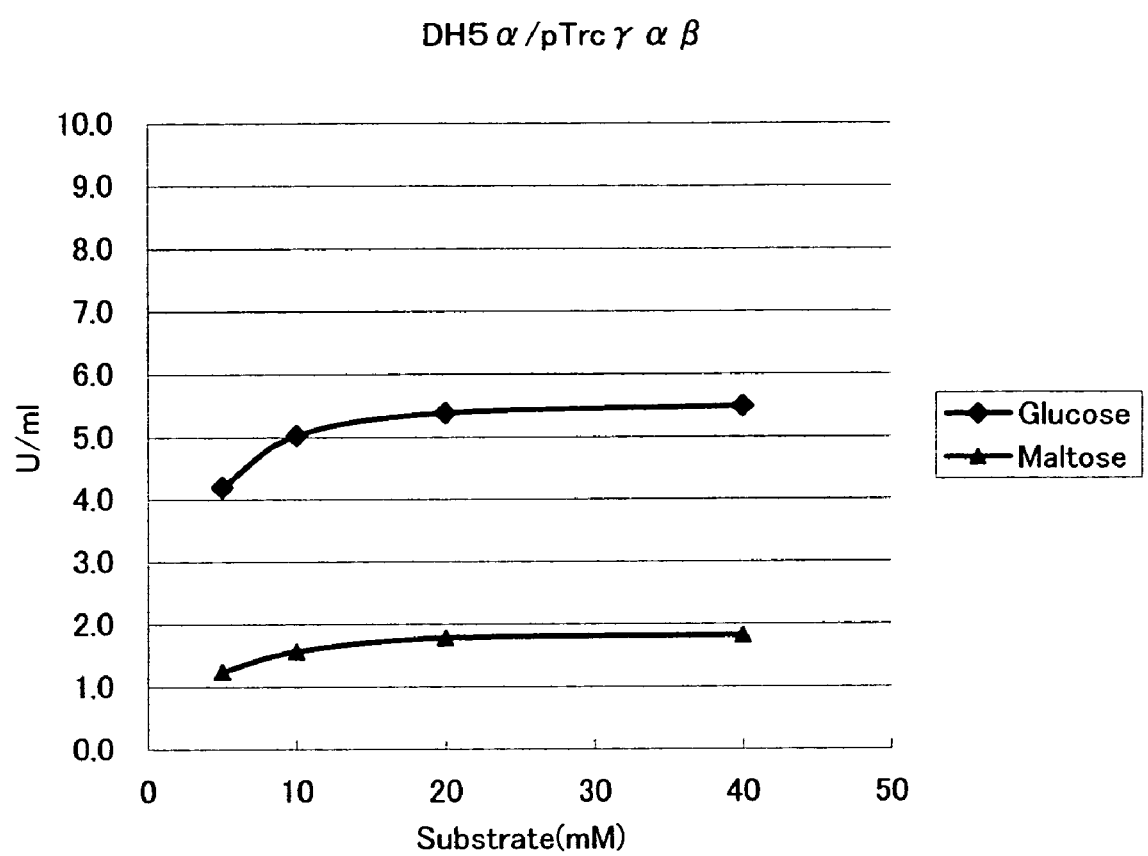
FIG. 3 shows dehydrogenase activities of DH5α/pTrc99Aγαβ for glucose and maltose as substrates.
Figure 4:
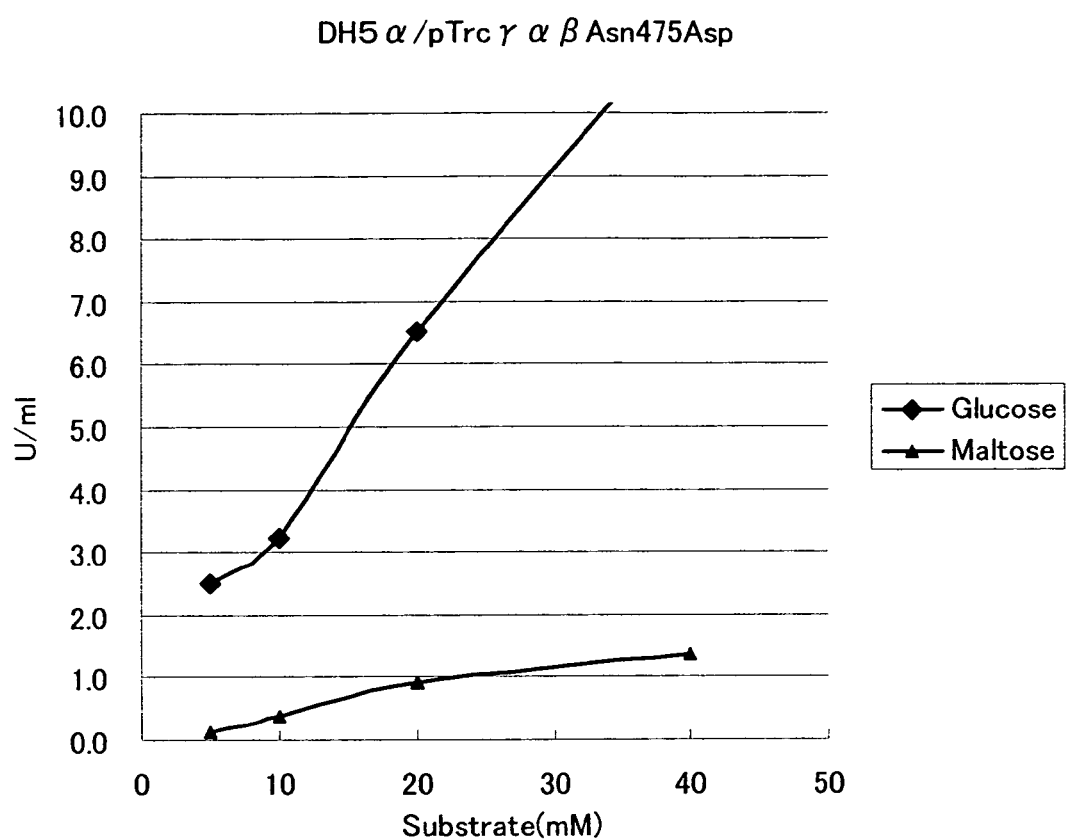
FIG. 4 shows dehydrogenase activities of DH5α/pTrcγαβAsn475Asp for glucose and maltose as substrates.
Figure 5:
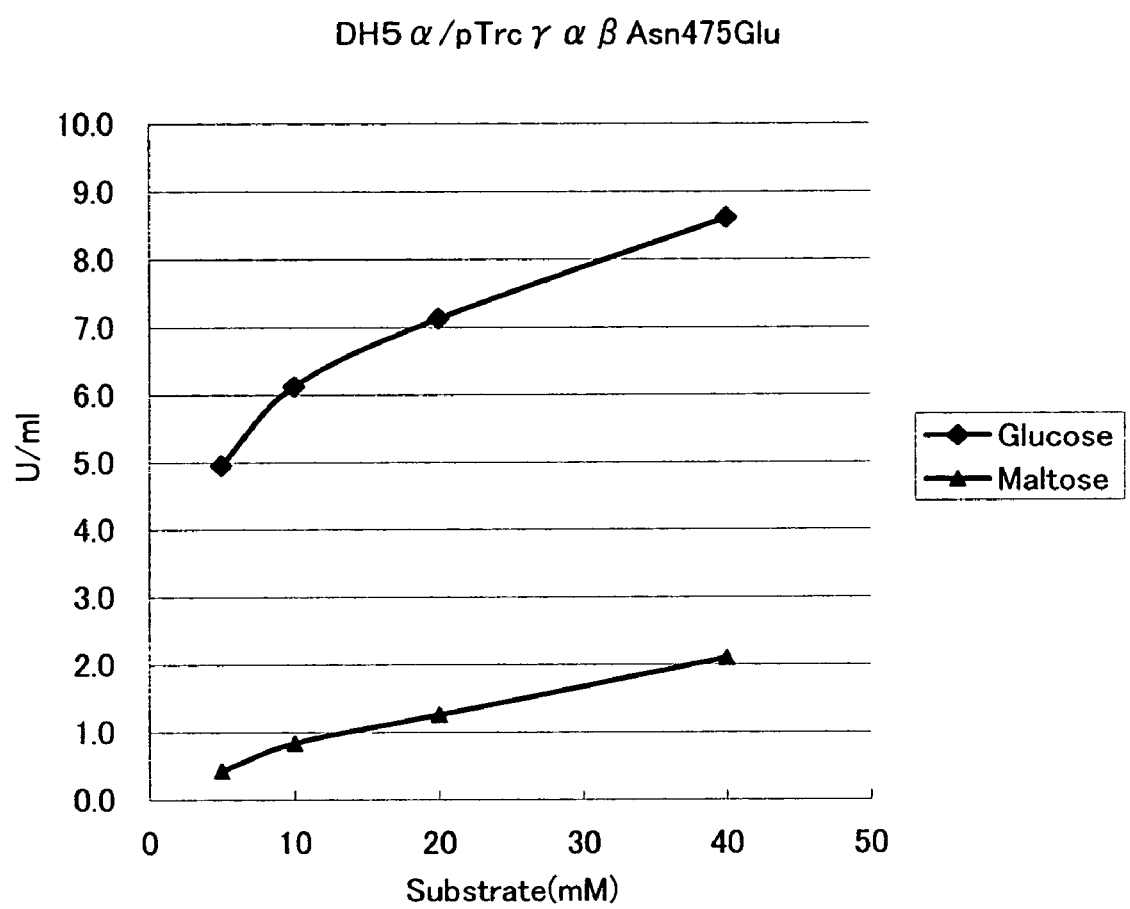
FIG. 5 shows dehydrogenase activities of DH5α/pTrcγαβAsn475Glu for glucose and maltose as substrates.

Hereafter, the present invention will be explained in detail.

The mutant GDH of the present invention is produced by introducing a specific mutation into a wild type GDH. Examples of the wild type GDH include GDHs produced by *Burkholderia cepacia*. Examples of the GDHs produced by *Burkholderia cepacia* include GDHs produced by the *Burkholderia cepacia* KS1, JCM2800 and JCM2801 strains. The KS1 strain was deposited at the independent administrative corporation, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Sep. 25, 2000 and given an accession number FERM BP-7306. The JCM2800 and JCM2801 strains are stored at the independent administrative corporation, RIKEN, Bioresource Center, Japan Collection of Microorganisms (JCM).

The nucleotide sequence of a chromosomal DNA fragment containing the GDH α-subunit gene and a part of the β-subunit gene of the KS1 strain is shown in SEQ ID NO: 4 (U.S. Patent Application No. 2004/0023330). Three open reading frames (ORF) exist in this nucleotide sequence, the second and third ORFs from the 5' end side code for the α-subunit (SEQ ID NO: 13) and the β-subunit (SEQ ID NO: 14), respectively. Further, it is inferred that the first ORF codes for the γ-subunit (SEQ ID NO: 12). Further, the nucleotide sequence of a fragment containing the full-length β-subunit gene is shown in SEQ ID NO: 15. Further, the amino acid sequence of the β-subunit is shown in SEQ ID NO: 16. It is inferred that the amino acid numbers 1 to 22 in SEQ ID NO: 16 correspond to a signal peptide. Although the first amino acid residues are Val in SEQ ID NOS: 15 and 16, they are very likely to be Met and may be eliminated after translation.

The mutant GDH of the present invention may consist of the α-subunit alone, a complex comprising the α-subunit and the β-subunit, or a complex comprising the α-subunit, β-subunit and γ-subunit. The mutant GDH of the present invention is obtained by introducing a specific mutation into the α-subunit in any case, and may have a conservative mutation in addition to the above specific mutation. Further, the other subunits may be of a wild type or have a conservative mutation. The term "conservative mutation" means a mutation that does not substantially affect the GDH activity.

The mutant α-subunit of the present invention preferably has the amino acid sequence of SEQ ID NO: 13 except that it includes the specific mutation described later. Further, the mutant α-subunit may have the aforementioned conservative mutation so long as it has the GDH activity. That is, it may be a protein having an amino acid sequence of SEQ ID NO: 13 including substitution, deletion, insertion or addition of one or more amino acid residues in addition to the aforementioned specific mutation. SEQ ID NO: 13 shows an amino acid sequence that can be encoded by the nucleotide sequence of SEQ ID NO: 11. However, the methionine residue at the N-terminus may be eliminated after translation. The aforementioned term "one or several" preferably means a number of 1 to 10, more preferably 1 to 5, particularly preferably 1 to 3.

Further, the β-subunit typically has the amino acid sequence of SEQ ID NO: 16. However, so long as it functions as the β-subunit of GDH, it may be a protein having an amino acid sequence of the amino acid numbers 23 to 425 of SEQ ID NO: 16 including substitution, deletion, insertion or addition of one or more amino acid residues. The aforementioned term "one or several" preferably means a number of 1 to 20, more preferably 1 to 10, particularly preferably 1 to 5. The expression "functions as the GDH β-subunit" means to function as cytochrome C without degrading the enzymatic activity of GDH.

Specific examples of the wild type α-subunit gene include a DNA containing the nucleotide sequence corresponding to the nucleotide numbers 764 to 2380 of SEQ ID NO: 11. Further, the α-subunit gene may be a DNA having the nucleotide sequence corresponding to the nucleotide numbers 764 to 2380 in the nucleotide sequence of SEQ ID NO: 11 or a DNA which is hybridizable with a probe prepared from that sequence under a stringent condition and codes for a protein having the GDH activity.

Further, specific examples of the β-subunit gene include a DNA having the nucleotide sequence corresponding to the nucleotide numbers 187 to 1398 of SEQ ID NO: 9. Further, the β-subunit gene may be a DNA which has the nucleotide sequence corresponding to the nucleotide numbers 187 to 1398 of SEQ ID NO: 9, or a DNA which is hybridizable with a probe prepared from that sequence under a stringent condition and codes for a protein that can function as the β-subunit.

Examples of the aforementioned stringent condition include, for example, a condition under which DNAs having a homology of 70% or more, preferably 80% or more, more preferably 90% or more, particularly preferably 95% or more, hybridize with each other, and it is specifically exemplified by the condition of 1×SSC, 0.1% SDS at 60° C.

The α-subunit gene and the β-subunit gene can be obtained by, for example, PCR using chromosomal DNA of the Burkhorderia cepacia KS1 strain as a template. Primers for PCR can be prepared by chemical synthesis on the basis of the aforementioned nucleotide sequences. Further, they can also be obtained from chromosomal DNA of the Burkhorderia cepacia KS1 strain by hybridization using an oligonucleotide prepared on the basis of the aforementioned sequences as a probe. Further, variants thereof can also be similarly obtained from other strains of Burkhorderia cepacia. Examples of the other bacterial strains include the aforementioned JCM2800 and JCM2801 strains. The α-subunits of GDHs produced by these strains have homologies of 95.4 and 93.7%, respectively, to the α-subunit of the KS1 strain.

Further, even GDHs produced by other microorganisms can be used for the production of mutant GDH of the present invention so long as they have a structure and enzymological characteristics similar to those of GDH produced by Burkhorderia cepacia.

In the mutant GDH of the present invention, substrate specificity to glucose is improved by introducing a specific mutation into the aforementioned wild type GDH. The expression "substrate specificity to glucose is improved" means that reactivity to other sugars such as monosaccharides, disaccharide and oligosaccharides, for example, maltose, galactose, xylose and so forth, is decreased while the reactivity to glucose is substantially maintained, or reactivity to glucose is improved compared with reactivities to other sugars. For example, even if reactivity to glucose is decreased, but if reactivities to other sugars are decreased to a greater extent, substrate specificity to glucose is improved. Further, even if reactivities to other sugars are increased, but if substrate specificity to glucose is increased to a greater extent, substrate specificity to glucose is improved. Specifically, for example, if the ratio of specific activity for glucose and specific activity for another sugar, for example, maltose ((reactivity to another sugar/reactivity to glucose)×100) is decreased by 10% or more, preferably 20% or more, more preferably 50% or more, substrate specificity to L glucose is improved.

The aforementioned specific mutation means any one of amino acid substitution at position 472, amino acid substitution at position 475 and amino acid substitution at both positions 472 and 475 in the amino acid sequence of the SEQ ID NO: 13. More specific examples of the mutation include amino acid substitutions described below. The numerals shown below represent a position in the amino acid sequence, the amino acid residues represent an amino acid residue after substitution at the aforementioned position, and "+" means that two amino acid substitutions are simultaneously included. Among the following amino acid substitutions, amino acid substitutions at position 472 are listed in (A), amino acid substitutions at position 475 are listed in (B), and amino acid substitutions at both positions 472 and 475 are listed in (C). For example, "472Asn+475(Asp, Gly, His, Phe, Ser, Tyr)" means mutations for substitution of Asn for the amino acid residue at position 472 (Ala in the wild type), and substitution of Asp, Gly, His, Phe, Ser or Tyr for the amino acid residue at position 475 (Asn in the wild type).

(A) 472Arg, 472Asn, 472Asp, 472Cys, 472Glu, 472Gly, 472His, 472Ile, 472Leu, 472Met, 472Phe, 472Pro, 472Ser, 472Trp, 472Tyr, 472Val, (B) 475Asp, 475Cys, 475Glu, 475Gly, 475His, 475Met, 475Phe, 475Ser, 475Tyr, 475Val, (C) 472Arg+475(Asp, Glu, Gly, His, Phe, Ser, Tyr), 472Asn+475(Asp, Gly, His, Phe, Ser, Tyr), 472Asp+475(H is, Phe, Ser, Val), 472Cys+475(Asp, Gly, His, Phe, Ser), 472Glu+

475(Asp, Glu, Gly, His, Phe, Ser, Tyr), 472Gly+475(Asp, Cys, Gly, Met, Phe, Ser, Tyr), 472His+475(Cys, Glu, His, Met, Phe, Ser, Tyr), 472Ile+475(Asp, Cys, Glu, Gly, His, Met, Phe, Ser, Tyr), 472Leu+475(Asp, Gly, His, Phe, Ser, Tyr), 472Met+475(Asp, Gly, His, Phe, Ser), 472Phe+475 (Asp, Glu, Gly, His, Met, Phe, Ser, Tyr), 472Pro+475His 472Ser+475(Asp, Glu, Gly, His, Phe, Ser), 472Trp+475(H is, Phe, Ser), 472Tyr+475(Asp, His, Phe, Ser), 472Val+475 (Asp, Glu, Gly, His, Phe, Ser).

Among the aforementioned amino acid substitutions, preferred are listed below.

(D) 472Arg, 472Asn, 472Asp, 472Glu, 472Gly, 472Phe, 472Pro, (E) 475Asp, 475Cys, 475Glu, 475Gly, 475Met, 475Phe (F) 472Arg+475(Asp, Gly, His, Phe), 472Asn+475(Gly, His, Phe, Tyr), 472Asp+475(H is, Ser), 472Cys+475(Gly, His, Phe), 472Glu+475(Glu, His, Phe, Tyr), 472Gly+475(Asp, Phe, Tyr), 472His+475(H is, Ser), 472Ile+475(Asp, Glu, Gly, His, Ser), 472Leu+475(Gly, His, Phe, Tyr), 472Met+475(Asp, Gly, His, Phe), 472Phe+475(Asp, Glu, Gly, His, Phe, Ser, Tyr), 472Ser+475(Glu, Gly, His, Phe), 472Trp+475(H is, Phe), 472Tyr+475His, 472Val+475(Asp, Glu, Gly, His, Phe).

The positions of the aforementioned amino acid substitution mutations are those in SEQ ID NO: 13, that is, the amino acid sequence of the wild type GDH α-subunit of the *Burkholderia cepacia* KS1 strain, and in a GDH α-subunit homologue or variant having an amino acid sequence containing substitution, deletion, insertion or addition of one or more amino acid residues in the amino acid sequence of SEQ ID NO: 13 in addition to the aforementioned specific mutations, the positions are those corresponding to the positions of aforementioned amino acid substitutions determined by alignment with the amino acid sequence of SEQ ID NO: 13. For example, in a conservative GDH α-subunit variant having deletion of one amino acid residue in the region of 1st to 471st positions, the 472nd and 475th positions represent the 471st and 474th positions in the variant.

The inventors of the present invention investigated the region of glucose dehydrogenase involved in binding to FAD and neighboring regions as positions for introduction of the mutation for improving the substrate specificity. As the region involved in binding to FAD, the FAD neighboring region (FAD-covering lid) or FAD-binding domain, specifically, regions corresponding to the amino acid sequences of SEQ ID NOS: 1 to 4, were contemplated.

The term "regions corresponding to amino acid sequences" means, in the GDH α-subunit of the *Burkholderia cepacia* KS1 strain having the amino acid sequence of SEQ ID NO: 13, regions having the amino acid sequence of SEQ ID NO: 1, 2 or 4, that is, regions of the amino acid numbers 88 to 92, 57 to 61, and 470 to 504 in SEQ ID NO: 13. Further, in the GDH α-subunit having an amino acid sequence homologous to the amino acid sequence of SEQ ID NO: 13, the regions are those corresponding to the regions of the amino acid numbers 88 to 92, 57 to 61 or 470 to 504 in the GDH α-subunit of the aforementioned *Burkholderia cepacia* KS1 strain determined by alignment with the amino acid sequence of SEQ ID NO: 13.

The inventors of the present invention compared the amino acid sequences of the GMC oxidoreductase family enzymes using FAD as a coenzyme, sorbitol dehydrogenase of *Gluconobacter oxydans* (GenBank accession AB039821), 2-ketoglutarate dehydrogenase of *Erwinia herbicola* (GenBank accession AF068066), cellobiose dehydrogenase (CDH) of *Phanerochaete chrysosporium* (J. Mol. Biol., 315(3), 421-34 (2002)), cholesterol oxidase (COD) of *Streptomyces* species (J. Struct. Biol. 116(2), 317-9 (1996)), and glucose oxidase of *Penicillium amagasakiens* (Eur. J. Biochem. 252, 90-99 (1998)), and found a region in which the FAD-binding domain and FAD-covering lid were conserved and a region in which proline was conserved, which is an amino acid residue involved in folding of proteins. Then, they examined the possibility of improving substrate specificity by modifying sequences in the vicinity of the borders between these regions and other regions. As a result, they confirmed that the substrate specificity could be improved by mutations of the aforementioned amino acid residues.

A GDH α-subunit having a desired mutation can be obtained by introducing a nucleotide mutation corresponding to a desired amino acid mutation into a DNA coding for the GDH α-subunit (α-subunit gene) by site-directed mutagenesis and expressing the obtained mutant DNA by using a suitable expression system. Further, a mutant GDH complex can be obtained by expressing a DNA coding for the mutant GDH α-subunit together with a DNA coding for the β-subunit (β-subunit gene) or the β-subunit gene and a DNA coding for the γ-subunit (γ-subunit gene). For the introduction of a mutation into a DNA coding for the GDH α-subunit, a polycistronic DNA fragment coding for the GDH α-subunit, γ-subunit and β-subunit in this order may also be used.

Substrate specificities to sugars of the GDH α-subunit or the GDH complex introduced with the mutation can be determined by examining reactivities to various sugars by the methods described in the examples and comparing them with reactivities of a wild type GDH α-subunit or a wild type GDH complex.

A polycistronic DNA fragment coding for the γ-subunit, α-subunit and β-subunit in this order can be obtained by, for example, PCR using chromosomal DNA of the *Burkhorderia cepacia* KS1 strain as a template and oligonucleotides having the nucleotide sequences of SEQ ID NOS: 12 and 13 as primers (see the examples described later).

Examples of vectors used for obtaining the genes of GDH subunits, introduction of mutation, expression of the genes and so forth include vectors that function in *Escherichia* bacteria, and specific examples thereof include pTrc99A, pBR322, pUC18, pUC118, pUC19, pUC119, pACYC184, pBBR122 and so forth. Examples of the promoters used for expression of genes include lac, trp, tac, trc, $P_L$, tet, PhoA and so forth. Further, insertion of these genes into a vector and ligation of a promoter can be performed in one step by inserting the α-subunit gene or other subunit genes at a suitable site in an expression vector containing the promoter. Examples of such an expression vector include pTrc99A, pBluescript, pKK223-3 and so forth.

Further, the α-subunit gene or other subunit genes may be incorporated into chromosomal DNA of a host microorganism in an expressible form.

Examples of the method for transforming a microorganism with a recombinant vector include, for example, the competent cell method using a calcium treatment, protoplast method, electroporation and so forth.

Examples of the host microorganism include *Bacillus* bacteria such as *Bacillus subtilits*, yeast such as *Saccharomyces cerevisiae* and filamentous fungi such as *Aspergillus niger*. However, the host microorganism is not limited to these examples, and host microorganisms suitable for producing foreign proteins can be used.

The mutant α-subunit, the mutant GDH complex, and the microorganism expressing them of the present invention can be used as an enzyme electrode of a glucose sensor or a component of a glucose assay kit. A glucose sensor and glucose assay kit using the wild type GDH of *Burkholderia* cepacia are described in U.S. Patent No. 2004/0023330A1. The mutant GDH of the present invention can also be used in a similar manner.

EXAMPLES

The present invention will be explained more specifically with reference to the following examples. However, the scope of the present invention is not limited to these examples.

Example 1

Plasmids expressing GDH of Burkhorderia cepacia

As plasmids expressing GDH of Burkhorderia cepacia, a plasmid expressing the GDH α-subunit and γ-subunit and a plasmid expressing the α-subunit, β-subunit and γ-subunit were prepared.

<1>Plasmid Expressing GDH α-Subunit and γ-Subunit

As a plasmid expressing the α-subunit and γ-subunit, plasmid pTrc99A/γ+α described in WO02/036779 was used. This plasmid is a plasmid obtained by inserting a DNA fragment sequentially containing the GDH γ-subunit structural gene and the α-subunit structural gene isolated from chromosomal DNA of the Burkhorderia cepacia KS1 strain (FERM BP-7306) into the vector pTrc99A (Pharmacia) at the NcoI/HindIII site as a cloning site thereof. The GDHγα gene in this plasmid is regulated by the trc promoter. pTrc99A/γ+α has an ampicillin resistance gene.

<2>Plasmid Expressing GDH α-Subunit, β-Subunit and γ-Subunit

A plasmid expressing the GDH α-subunit, β-subunit and γ-subunit was prepared as follows.

(1) Preparation of Chromosomal DNA from Burkhorderia cepacia KS1 Strain

A chromosomal gene was prepared from the Burkhorderia cepacia KS1 strain in a conventional manner. That is, the TL liquid medium (10 g of polypeptone, 1 g of yeast extract, 5 g of NaCl, 2 g of $KH_2PO_4$, 5 g of glucose in 1 L, pH 7.2) was used, and cells of the strain was shaken overnight in the medium at 34° C. The grown cells were collected by centrifugation. The cells were suspended in a solution containing 10 mM NaCl, 20 mM Tris-HCl (pH 8.0), 1 mM EDTA, 0.5% SDS and 100 µg/ml of proteinase K and treated at 50° C. for 6 hours. To the mixture was added an equal volume of phenol-chloroform, and the mixture was stirred at room temperature for 10 minutes. Then, the supernatant was collected by centrifugation. To the supernatant was added sodium acetate at a final concentration of 0.3 M, and 2-fold volume of ethanol was overlaid to precipitate chromosomal DNA in the intermediate layer. The DNA was collected with a glass rod, washed with 70% ethanol, and then dissolved in a suitable volume of TE buffer to obtain a chromosomal DNA solution.

(2) Preparation of DNA Fragment Coding for GDH γ-subunit, α-subunit and β-subunit A DNA fragment coding for the GDH γ-subunit, α-subunit and β-subunit was amplified by PCR using the aforementioned chromosomal DNA as a template and oligonucleotides having the following sequences as primers.

```
[Forward primer]
                                            (SEQ ID NO: 5)
5'-CATGCCATGGCACACAACGACAACAC-3'

[Reverse primer]
                                            (SEQ ID NO: 6)
5'-GTCGACGATCTTCTTCCAGCCGAACATCAC-3'
```

The C-terminus side of the amplified fragment was blunt-ended, the N-terminus side was digested with NcoI, and the fragment was ligated to similarly treated pTrc99A (Pharmacia). E. coli DH5α was transformed with the obtained recombinant vector, and colonies grown on the LB agar medium containing 50 µg/mL of ampicillin were collected. The obtained transformants were cultured in the liquid LB medium, plasmids were extracted, and DNA fragments inserted in the plasmids were analyzed. As a result, an inserted fragment of about 3.8 kb was confirmed. This plasmid was designated as pTrc99Aγαβ. The structural genes of GDH in this plasmid are regulated by the trc promoter. pTrc99Aγαβ has an ampicillin resistance gene and a kanamycin resistance gene.

Example 2

Introduction of Mutation into GDH α-subunit Gene

By using a commercially available site-directed mutatgenesis kit (QuikChangeII Site-Directed Mutagenesis Kit, Stratagene), the codon of aspartic acid (GAT) or glutamic acid (GAA) was substituted for the codon of the 475th asparagine (AAT) in the GDH α-subunit gene contained in the plasmids pTrc99A/γ+α and pTrc99Aγαβ described in Example 1. As primers, the following oligonucleotides were used. Hereinafter, substitution of an aspartic acid residue for the 475th asparagine residue is referred to as "Asn475Asp", and substitution of a glutamic acid residue for the 475th asparagine residue is referred to as "Asn475Glu".

```
Primers for Asn475Asp substitution
[Forward primer]
                                            (SEQ ID NO: 7)
5'-CGCGCCGAACGATCACATCACGGGC-3'

[Reverse primer]
                                            (SEQ ID NO: 8)
5'-GCCCGTGATGTGATCGTTCGGCGCG-3'

Primers for Asn475Glu substitution
[Forward primer]
                                            (SEQ ID NO: 9)
5'-GAATTCGCGCCGAACGAACACATCAGGGGCTCG-3'

[Reverse primer]
                                            (SEQ ID NO: 10)
5'-CGAGCCCGTGATGTGTTCGTTCGGCGCGAATTC-3'
```

PCR was performed by using the following reaction composition. After a reaction at 95° C. for 30 seconds, a cycle of reactions at 95° C. for 30 seconds, 55° C. for 1 minute and 68° C. for 8 minutes was repeated 15 times. Then, after a reaction at 68° C. for 30 minutes, the reaction mixture was maintained at 4° C.

| [Reaction mixture composition] | |
|---|---|
| Template DNA (5 ng/μl) (pTrc99A/γ + α and pTrc99Aγαβ) | 2 μl |
| 10× Reaction buffer | 5 μl |
| Forward primer (100 ng/μl) | 1.25 μl |
| Reverse primer (100 ng/μl) | 1.25 μl |
| dNTP | 1 μl |
| Distilled water | 38.5 μl |
| DNA polymerase | 1 μl |
| Total | 50 μl |

After PCR, 0.5 μl of DNA polymerase I was added to the reaction mixture, and the mixture was incubated at 37° C. for 1 hour to decompose the template plasmid.

Competent cells of *Escherichia coli* DH5α (supE44, ΔlacU169 (φ+80lacZΔM15), hsdR17, recA1, endA1, gyrA96, thi-1, relA1) were transformed with the obtained reaction mixture. Plasmid DNA was prepared from several colonies grown on the LB agar medium (1% bacto tryptone, 0.5% yeast extract, 1% sodium chloride, 1.5% agar) containing ampicillin (50 μg/ml) and kanamycin (30 μg/ml), and sequence analysis was performed to confirm that the objective mutations had been introduced into the GDH α-subunit gene. pTrc99A/γ+α and pTrc99Aγαβ introduced with the Asn475Asp mutation were designated as pTrcγαAsn475Asp and pTrcγαβAsn475Asp, respectively. Further, pTrc99A/γ+α and pTrc99Aγαβ introduced with the Asn475Glu mutation were designated as pTrcγαAsn475Glu and pTrcγαβAsn475Glu, respectively.

Example 3

Analysis of Substrate Specificity of Mutant GDHs

Mutant GDHs were produced by using the mutant GDH expressing plasmids obtained in Example 2, and substrate specificities thereof were examined.

(1) Culture

The *Escherichia coli* DH5a strain introduced with pTrcγαAsn475Glu and pTrcγαβAsn475Glu were each cultured overnight at 37° C. in 2 ml of the LB medium (containing 50 μg/ml of ampicillin and 30 μg/ml of kanamycin) in an L-shaped tube with shaking. These culture broths were inoculated in 150 ml of the LB medium (containing 50 μg/ml of ampicillin and 30 μg/ml of kanamycin) contained in a 500-ml Sakaguchi flask, and the cells were cultured at 37° C. with shaking. After 3 hours from the start of culture, isopropyl-β-D-thiogalactopyranoside (IPTG) was added at a final concentration of 0.1 mM, and the cells were further cultured for 2 hours.

(2) Preparation of Enzyme Samples

The cells were collected from each culture broth obtained as described above, washed, then suspended in 10 mM potassium phosphate buffer (PPB, pH 7.0) containing 1 ml of 0.2% Triton X-100 per 0.3 mg of wet cells, and disrupted by ultrasonication. This suspension was centrifuged (10000 rpm, 10 min, 4° C.) to remove the residues, then the supernatant was ultracentrifuged (50,000 r.p.m., 60 min, 4° C.), and the obtained supernatant (water-soluble fraction) was used as a crude enzyme sample. Further, this sample was purified by usual hydrophobic chromatography (column: Octyl Sepharose, Amersham Biosciences) and ion exchange chromatography (Q-Sepharose, Amersham Biosciences) to obtain a purified enzyme sample. The objective enzyme fraction was determined by using GDH activity as an index.

(3) Measurement of GDH Activity

To 8 μl of the aforementioned purified enzyme sample was added 8 μl of a reagent for measuring activity (solution obtained by adding 10 mM PPB containing 0.2% (w/v) Triton X-100 to 12 μl of 600 mM methylphenazine methosulfate (PMS) and 120 μl of 6 mM 2,6-dichrolophenol-indophenol (DCIP) to make a total volume of 480 μl). This mixture was preincubated at each reaction temperature for one minute by using an aluminum block thermostatic chamber, then 8 μl of a substrate (glucose or maltose) at each concentration or distilled water was quickly added to the mixture, and the mixture was stirred. Absorbance at 600 nm as the DCIP-originated absorption wavelength was measured by using a spectrophotometer. The final concentrations of the reagents, DCIP and PMS, were 0.06 and 0.6 mM, respectively. The final concentrations of the substrate were 40, 20, 10 and 5 mM.

The results are shown in Table 1 and FIGS. 1 to 5.

TABLE 1

| | Substrate concentration | Activity (U/ml) | |
|---|---|---|---|
| | mM | Glucose | Maltose |
| pTrc99A/γ + α | 40 | 1.65 | 1.01 |
| | 20 | 1.70 | 1.03 |
| | 10 | 1.71 | 1.07 |
| | 5 | 1.57 | 0.72 |
| pTrcγαAsn475Asp | 40 | 19.46 | 1.30 |
| | 20 | 7.75 | 0.67 |
| | 10 | 4.15 | 0.21 |
| | 5 | 2.53 | 0.00 |
| pTrc99Aγαβ | 40 | 5.49 | 1.82 |
| | 20 | 5.38 | 1.78 |
| | 10 | 5.03 | 1.57 |
| | 5 | 4.20 | 1.24 |
| pTrcγαβAsn475Asp | 40 | 11.57 | 1.35 |
| | 20 | 6.53 | 0.93 |
| | 10 | 3.21 | 0.39 |
| | 5 | 2.50 | 0.13 |
| pTrcγαβAsn475Glu | 40 | 8.62 | 2.10 |
| | 20 | 7.13 | 1.26 |
| | 10 | 6.12 | 0.84 |
| | 5 | 4.95 | 0.43 |

As clearly seen form these results, it is evident that all the mutant GDHs have reduced reactivity to maltose while maintaining reactivity to glucose, that is, their specificity to glucose is improved.

Example 4

Introduction of Mutation into GDH α-Subunit Gene

Mutations were introduced into the GDH α-subunit gene contained in pTrc99Aγαβ obtained in Example 1 at the 475th position and neighboring positions, and substrate specificity of the mutant enzymes was evaluated. Mutations were introduced in the same manner as in Example 2. Primers for introducing mutations were prepared as follows. In the basic primers (wild type) shown in FIG. 6 (forward primer: SEQ ID NO: 17, reverse primer: SEQ ID NO: 18), codons were changed at predetermined positions (472nd and 475th) as shown in the codon change table mentioned in FIG. 6 to prepare primers for introducing various mutations.

Example 5

Analysis of Substrate Specificity of Mutant GDHs

Mutant GDHs were produced in the same manner as in Example 3 by using the mutant GDH expressing plasmids obtained in Example 4, and substrate specificities thereof were examined. The enzymatic activity was examined by using crude enzyme samples. The specific activity for glucose, specific activity for maltose and reaction ratio (specific activity for maltose/specific activity for glucose, unit is U/ml.) of each mutant GDH are shown in Tables 2 to 7. When the specific activity for glucose was 0.5 U/ml or lower, it was judged as no activity, and such a result was indicated with "−" in the tables.

As a result, for the 475th position, it was confirmed that substitutions other than the substitution of aspartic acid (GAT) or glutamic acid (GAA) for asparagine performed in Example 2 also had an effect of improving the substrate characteristics. Further, it was found that substitution of another amino acid for asparagine (AAC) at the 472nd position in the vicinity of the 475th position could also improve the substrate characteristics. Further, it was also found that a combination of the amino acid substitutions at the 472nd and 475th positions could synergistically improve the substrate characteristics.

TABLE 2 substrate conc.: 10 mM
specific activity to glucose (U/ml broth)

| 472 ↓ | Ala | Arg | Asn | Asp | Cys | Glu | Gln | Gly | His | Ile |
|---|---|---|---|---|---|---|---|---|---|---|
| Ala | — | — | 7 | 6.5 | 24 | 7 | — | 4.75 | 0.85 | — |
| Arg | — | — | 6 | 2.35 | — | 1.5 | — | 2.3 | 2.4 | — |
| Asn | — | — | 6.2 | 0.75 | — | — | — | 2.3 | 4.7 | — |
| Asp | — | — | 1.35 | — | — | — | — | — | 1.75 | — |
| Cys | — | — | 6.45 | 0.75 | — | — | — | 4 | 4.3 | — |
| Glu | — | — | 6.1 | 2.15 | — | 1.2 | — | 3.45 | 4.65 | — |
| Gln | — | — | — | — | — | — | — | — | — | — |
| Gly | — | — | 6.35 | 0.6 | 1 | — | — | 6.85 | — | — |
| His | — | — | 4.45 | — | 0.85 | 2.75 | — | — | 4.4 | — |
| Ile | — | — | 7.25 | 2.4 | 0.75 | 2.2 | — | 2.1 | 4.4 | — |
| Leu | — | — | 6.35 | 0.75 | — | — | — | 1.9 | 5.65 | — |
| Lys | — | — | — | — | — | — | — | — | — | — |
| Met | — | — | 5.9 | 1.85 | — | — | — | 3.3 | 5.8 | — |
| Phe | — | — | 6.79 | 0.65 | — | 0.55 | — | 1.75 | 6.25 | — |
| Pro | — | — | 1.2 | — | — | — | — | — | 2.3 | — |
| Ser | — | — | 6.1 | 1.1 | — | 2.45 | — | 4.25 | 4 | — |
| Thr | — | — | — | — | — | — | — | — | — | — |
| Trp | — | — | 4.55 | — | — | — | — | — | 6.3 | — |
| Tyr | — | — | 4.35 | 0.5 | — | — | — | — | 5.75 | — |
| Val | — | — | 5.75 | 2.2 | — | 0.85 | — | 2.5 | 5.9 | — |

TABLE 3 substrate conc.: 10 mM
specific activity to maltose (U/ml broth)

| 472 ↓ | Ala | Arg | Asn | Asp | Cys | Glu | Gln | Gly | His | Ile |
|---|---|---|---|---|---|---|---|---|---|---|
| Ala | — | — | 3.5 | 1 | 0.55 | 1.5 | — | 1.35 | 0.8 | — |
| Arg | — | — | 0.85 | 0.25 | — | 0.35 | — | 0.25 | 0.35 | — |
| Asn | — | — | 0.75 | 0.21 | — | — | — | 0.28 | 0.44 | — |
| Asp | — | — | 0.1 | — | — | — | — | — | 0.25 | — |
| Cys | — | — | 1.2 | 0.18 | — | — | — | 0.2 | 0.41 | — |
| Glu | — | — | 0.7 | 0.85 | — | 0.15 | — | 0.35 | 0.41 | — |
| Gln | — | — | — | — | — | — | — | — | — | — |
| Gly | — | — | 0.8 | 0.08 | 0.3 | — | — | 1.55 | — | — |
| His | — | — | 1.05 | — | 0.2 | 0.5 | — | — | 0.5 | — |
| Ile | — | — | 0.85 | 0.2 | 0.1 | 0.2 | — | 0.33 | 0.45 | — |
| Leu | — | — | 1.2 | 0.2 | — | — | — | 0.3 | 0.45 | — |
| Lys | — | — | — | — | — | — | — | — | — | — |
| Met | — | — | 1.1 | 0.25 | — | — | — | 0.34 | 0.45 | — |
| Phe | — | — | 0.81 | 0.09 | — | 0.09 | — | 0.25 | 0.45 | — |
| Pro | — | — | 0.15 | — | — | — | — | — | 0.6 | — |
| Ser | — | — | 1.25 | 0.24 | — | 0.25 | — | 0.5 | 0.4 | — |
| Thr | — | — | — | — | — | — | — | — | — | — |
| Trp | — | — | 1.1 | — | — | — | — | — | 0.6 | — |
| Tyr | — | — | 1.05 | 0.14 | — | — | — | — | 0.35 | — |
| Val | — | — | 1.1 | 0.2 | — | 0.1 | — | 0.22 | 0.49 | — |

TABLE 4 substrate conc.: 10 mM
maltose/glucose (reaction ratio)

| 472 ↓ | 475 → | | | | | | | | | |
|---|---|---|---|---|---|---|---|---|---|---|
| | Ala | Arg | Asn | Asp | Cys | Glu | Gln | Gly | His | Ile |
| Ala | — | — | 50% | 15% | 23% | 21% | — | 28% | 94% | — |
| Arg | — | — | 14% | 10% | — | 23% | — | 11% | 14% | — |
| Asn | — | — | 12% | 27% | — | — | — | 12% | 9% | — |
| Asp | — | — | 7% | — | — | — | — | — | 14% | — |
| Cys | — | — | 19% | 24% | — | — | — | 5% | 10% | — |
| Glu | — | — | 11% | 40% | — | 13% | — | 10% | 9% | — |
| Gln | — | — | — | — | — | — | — | — | — | — |
| Gly | — | — | 13% | 13% | 30% | — | — | 23% | — | — |
| His | — | — | 24% | — | 24% | 18% | — | — | 11% | — |
| Ile | — | — | 12% | 8% | 13% | 9% | — | 16% | 10% | — |
| Leu | — | — | 19% | 27% | — | — | — | 16% | 8% | — |
| Lys | — | — | — | — | — | — | — | — | — | — |
| Met | — | — | 19% | 14% | — | — | — | 10% | 8% | — |
| Phe | — | — | 12% | 13% | — | 15% | — | 14% | 7% | — |
| Pro | — | — | 13% | — | — | — | — | — | 26% | — |
| Ser | — | — | 20% | 22% | — | 10% | — | 12% | 10% | — |
| Thr | — | — | — | — | — | — | — | — | — | — |
| Trp | — | — | 24% | — | — | — | — | — | 10% | — |
| Tyr | — | — | 24% | 27% | — | — | — | — | 6% | — |
| Val | — | — | 19% | 9% | — | 12% | — | 9% | 8% | — |

Total: 60

TABLE 5 substrate conc.: 10 mM
specific activity to glucose (U/ml broth)

| 472 ↓ | 475 → | | | | | | | | | |
|---|---|---|---|---|---|---|---|---|---|---|
| | Leu | Lys | Met | Phe | Pro | Ser | Thr | Trp | Tyr | Val |
| Ala | — | — | 1.6 | 1.2 | — | 0.3 | — | — | 1.05 | 1.15 |
| Arg | — | — | — | 4.1 | — | 4.25 | — | — | 2 | — |
| Asn | — | — | — | 2.5 | — | 5.25 | — | — | 1.3 | — |
| Asp | — | — | — | 2.65 | — | 3 | — | — | — | 6.2 |
| Cys | — | — | — | 2.85 | — | 4.5 | — | — | — | — |
| Glu | — | — | — | 1.4 | — | 6 | — | — | 1.9 | — |
| Gln | — | — | — | — | — | — | — | — | — | — |
| Gly | — | — | 3.1 | 3.25 | — | 8 | — | — | 0.5 | — |
| His | — | — | 1.1 | 1.9 | — | 6.6 | — | — | — | — |
| Ile | — | — | 2.7 | 2.95 | — | 7 | — | — | 3 | — |
| Leu | — | — | — | 1.6 | — | 5.5 | — | — | 2 | — |
| Lys | — | — | — | — | — | — | — | — | — | — |
| Met | — | — | — | 3.25 | — | 4.6 | — | — | — | — |
| Phe | — | — | 1.7 | 0.75 | — | 10.5 | — | — | 1.55 | — |
| Pro | — | — | — | — | — | — | — | — | — | — |
| Ser | — | — | — | 2.5 | — | 5.5 | — | — | — | — |
| Thr | — | — | — | — | — | — | — | — | — | — |
| Trp | — | — | — | 3.5 | — | 2.15 | — | — | — | — |
| Tyr | — | — | — | 0.85 | — | 3.85 | — | — | — | — |
| Val | — | — | — | 3.5 | — | 7 | — | — | 2.8 | — |

TABLE 6 substrate conc.: 10 mM
specific activity to maltose (U/ml broth)

| 472 ↓ | 475 → | | | | | | | | | |
|---|---|---|---|---|---|---|---|---|---|---|
| | Leu | Lys | Met | Phe | Pro | Ser | Thr | Trp | Tyr | Val |
| Ala | — | — | 0.5 | 0.35 | — | 0.25 | — | — | 0.65 | 1.05 |
| Arg | — | — | — | 0.26 | — | 1.7 | — | — | 0.33 | — |
| Asn | — | — | — | 0.45 | — | 1.1 | — | — | 0.18 | |
| Asp | — | — | — | 0.75 | — | 0.4 | — | — | | 3.3 |
| Cys | — | — | — | 0.2 | — | 0.95 | — | — | | |
| Glu | — | — | — | 0.15 | — | 1.15 | — | — | 0.07 | |

TABLE 6-continued substrate conc.: 10 mM
specific activity to maltose (U/ml broth)

475 →

| 472 ↓ | Leu | Lys | Met | Phe | Pro | Ser | Thr | Trp | Tyr | Val |
|---|---|---|---|---|---|---|---|---|---|---|
| Gln | — | — |  | — |  | — |  | — |  |  |
| Gly | — | — | 0.55 | 0.4 | — | 5 | — | — | 0.05 |  |
| His | — | — | 0.22 | 0.35 | — | 0.75 | — | — |  |  |
| Ile | — | — | 0.95 | 0.6 | — | 0.5 | — | — | 0.7 |  |
| Leu | — | — |  | 0.12 | — | 1.3 | — | — | 0.25 |  |
| Lys | — | — |  |  | — |  | — | — |  |  |
| Met | — | — |  | 0.2 | — | 1.1 | — | — |  |  |
| Phe | — | — | 0.75 | 0.07 | — | 0.65 | — | — | 0.2 |  |
| Pro | — | — |  |  | — |  | — | — |  |  |
| Ser | — | — |  | 0.2 | — | 1.3 | — | — |  |  |
| Thr | — | — |  |  | — |  | — | — |  |  |
| Trp | — | — |  | 0.2 | — | 0.55 | — | — |  |  |
| Tyr | — | — |  | 0.15 | — | 1.1 | — | — |  |  |
| Val | — | — |  | 0.2 | — | 1.2 | — | — |  |  |

TABLE 7 substrate conc.: 10 mM
maltose/glucose (reaction ratio)

475 →

| 472 ↓ | Leu | Lys | Met | Phe | Pro | Ser | Thr | Trp | Tyr | Val |
|---|---|---|---|---|---|---|---|---|---|---|
| Ala | — | — | 31% | 29% | — | 83% | — | — | 62% | 91% |
| Arg | — | — | — | 6% | — | 40% | — | — | 16% | — |
| Asn | — | — | — | 18% | — | 21% | — | — | 13% | — |
| Asp | — | — | — | 28% | — | 13% | — | — | — | 53% |
| Cys | — | — | — | 7% | — | 21% | — | — | — | — |
| Glu | — | — | — | 11% | — | 19% | — | — | 3% | — |
| Gln | — | — | — | — | — | — | — | — | — | — |
| Gly | — | — | 18% | 12% | — | 63% | — | — | 10% | — |
| His | — | — | 20% | 18% | — | 11% | — | — | — | — |
| Ile | — | — | 35% | 20% | — | 7% | — | — | 23% | — |
| Leu | — | — | — | 8% | — | 24% | — | — | 13% | — |
| Lys | — | — | — | — | — | — | — | — | — | — |
| Met | — | — | — | 6% | — | 24% | — | — | — | — |
| Phe | — | — | 44% | 9% | — | 6% | — | — | 13% | — |
| Pro | — | — | — | — | — | — | — | — | — | — |
| Ser | — | — | — | 8% | — | 24% | — | — | — | — |
| Thr | — | — | — | — | — | — | — | — | — | — |
| Trp | — | — | — | 6% | — | 26% | — | — | — | — |
| Tyr | — | — | — | 18% | — | 29% | — | — | — | — |
| Val | — | — | — | 6% | — | 17% | — | — | — | — |

Total: 60

Example 6

Evaluation of Purified Enzymes Based on SV Plot

Figure 7:
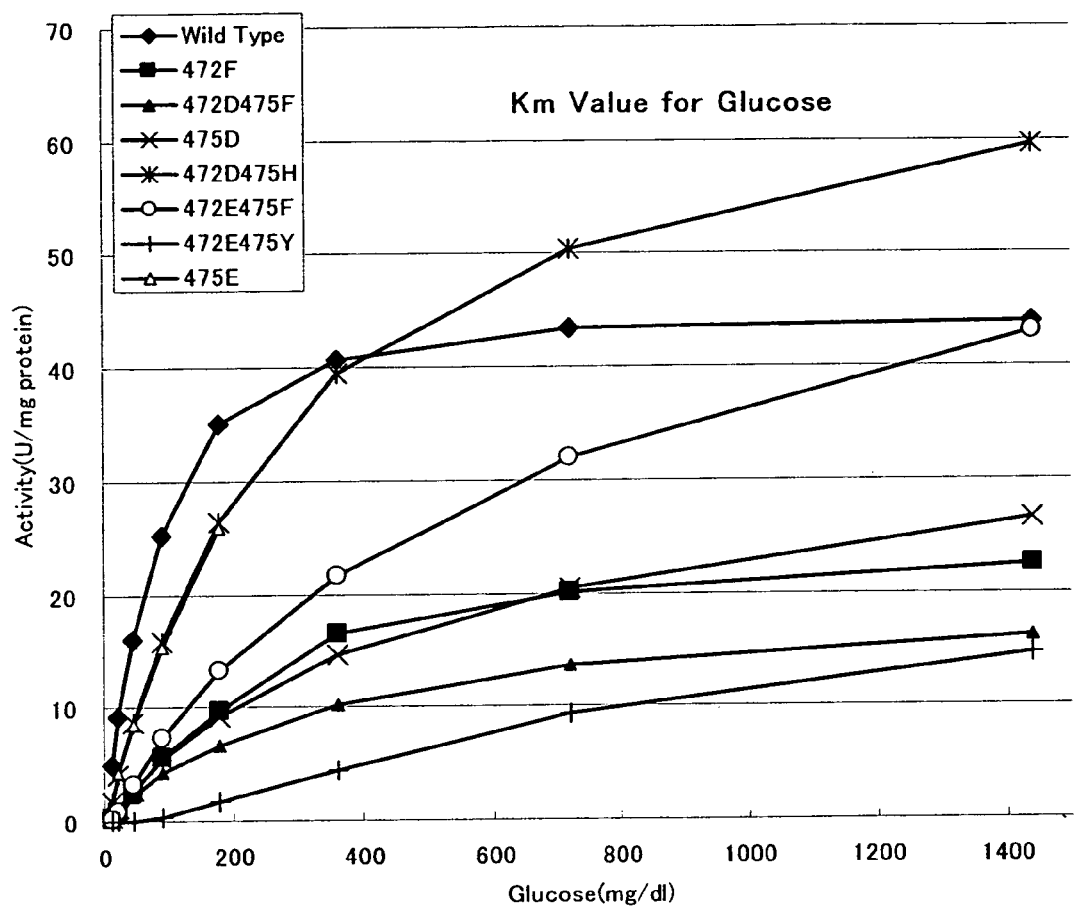
FIG. 7 shows SV plots of mutant GDHs.
Figure 8:
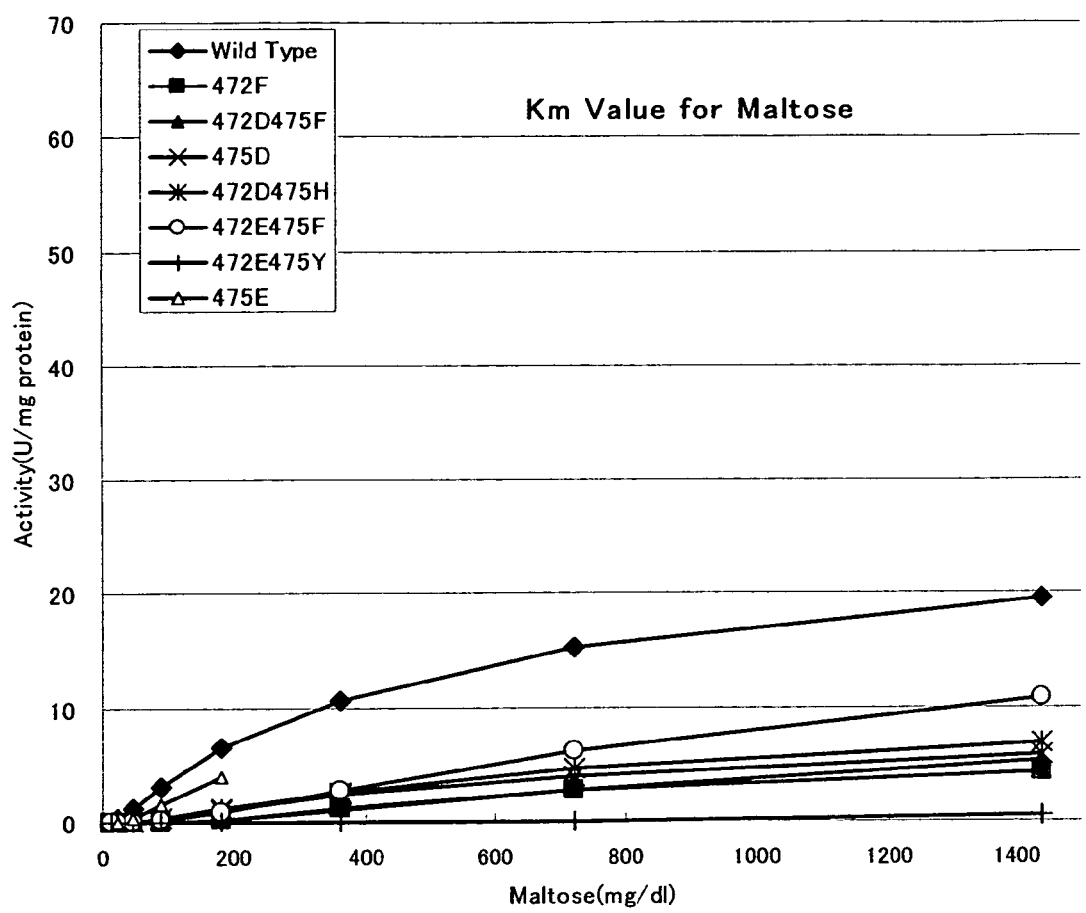
FIG. 8 shows SV plots of mutant GDHs.

SV plots were obtained for several mutant GDHs which showed improved substrate specificity in Example 5. Each mutant GDH was purified in the same manner as in Example 3. The results are shown in FIGS. 7 and 8 and Table 8.

As a result, it was confirmed that the reaction ratios (specific activity for maltose/specific activity for glucose) of the purified enzymes were also improved and became lower than that of the wild type at all the examined substrate concentrations. Further, since the results were substantially consistent with the measurement results using the crude enzyme solutions in Example 5, sufficient feasibility of screening for modified enzymes using crude enzymes could be confirmed. Further, modified enzymes to be used for a glucose sensor were selected from these candidates. For this purpose, since the blood maltose level elevates up to 200 mg/dl even at most, attentions were paid particularly to the reaction ratios at the substrate concentrations of 180 and 90 mg/dl. As a result, 472Asp475His was selected as a candidate of which reactivity to glucose was not so decreased compared with the wild type, and 472Glu475Tyr was selected as a candidate of which reactivity to glucose decreased but hardly reacted with maltose.

TABLE 8

Evaluation of characteristics of enzymes

| substrate conc. | 1440 | 720 | 360 | 180 | 90 | 45 | 22.5 | 11.25 | mg/dl |
|---|---|---|---|---|---|---|---|---|---|
| | | | | U/mg-p | | | | | |
| | | | | reactivity to glucose | | | | | |
| wild-type | 2198.8 | 2175.0 | 2035.8 | 1750.7 | 1264.6 | 803.7 | 461.7 | 244.0 | |
| 472F | 1123.3 | 1004.7 | 824.7 | 484.0 | 280.3 | 128.4 | 40.2 | 5.4 | |
| 472D475F | 811.5 | 678.6 | 512.5 | 328.9 | 215.3 | 107.3 | 33.7 | 4.1 | |
| 475D | 1324.4 | 1025.2 | 730.2 | 460.7 | 275.5 | 136.1 | 59.1 | 16.7 | |
| 472D475H | 2979.1 | 2522.1 | 1978.3 | 1322.9 | 795.0 | 430.8 | 207.1 | 82.9 | |
| 472E475F | 2153.8 | 1600.9 | 1079.9 | 667.3 | 366.0 | 165.6 | 46.6 | 7.0 | |
| 472E475Y | 734.4 | 466.8 | 219.5 | 88.2 | 17.4 | 2.4 | 0.8 | 0.2 | |
| 475E | | | | 1296.4 | 768.2 | 426.0 | 209.6 | | |
| | | | | reactivity to maltose | | | | | |
| wild-type | 975.5 | 763.8 | 532.1 | 323.9 | 157.3 | 59.7 | 14.1 | 1.3 | |
| 472F | 215.4 | 133.6 | 58.9 | 10.3 | 2.3 | 0.6 | 0.3 | 0.3 | |
| 472D475F | 265.4 | 138.9 | 51.2 | 7.7 | 1.2 | 0.3 | 0.2 | 0.2 | |
| 475D | 290.1 | 197.4 | 116.2 | 48.8 | 13.0 | 1.4 | 0.4 | 0.2 | |
| 472D475H | 342.6 | 228.5 | 131.9 | 59.6 | 17.1 | 3.6 | 0.9 | 0.4 | |
| 472E475F | 544.1 | 304.8 | 137.2 | 39.7 | 5.5 | 1.4 | 0.4 | 0.2 | |
| 472E475Y | 23.3 | 4.2 | 1.3 | 0.4 | 0.3 | 0.1 | 0.2 | 0.0 | |
| 475E | | | | 193.9 | 73.0 | 14.3 | 1.5 | | |
| | | | | reaction ratio: maltose/glucose | | | | | |
| wild-type | 44.4% | 35.1% | 26.1% | 18.5% | 12.4% | 7.4% | 3.1% | 0.5% | |
| 472F | 19.2% | 13.3% | 7.1% | 2.1% | 0.8% | 0.5% | 0.6% | 4.7% | |
| 472D475F | 32.7% | 20.5% | 10.0% | 2.3% | 0.6% | 0.3% | 0.5% | 3.8% | |
| 475D | 21.9% | 19.3% | 15.9% | 10.6% | 4.7% | 1.1% | 0.6% | 1.0% | |
| 472D475H | 11.5% | 9.1% | 6.7% | 4.5% | 2.1% | 0.8% | 0.4% | 0.4% | |
| 472E475F | 25.3% | 19.0% | 12.7% | 5.9% | 1.5% | 0.8% | 1.0% | 2.5% | |
| 472E475Y | 3.2% | 0.9% | 0.6% | 0.5% | 1.7% | 3.5% | 25.0% | 0.0% | |
| 475E | | | | 15.0% | 9.5% | 3.4% | 0.7% | | |

Example 7

Preparation of Calorimetric Sensor for Measuring Blood Sugar Levels using Mutant GDHs Colorimetric sensors for measuring blood sugar level were prepared by using 472Asp+475His type mutant GDH and 472Glu+475Tyr type mutant GDH.

Figure 9:
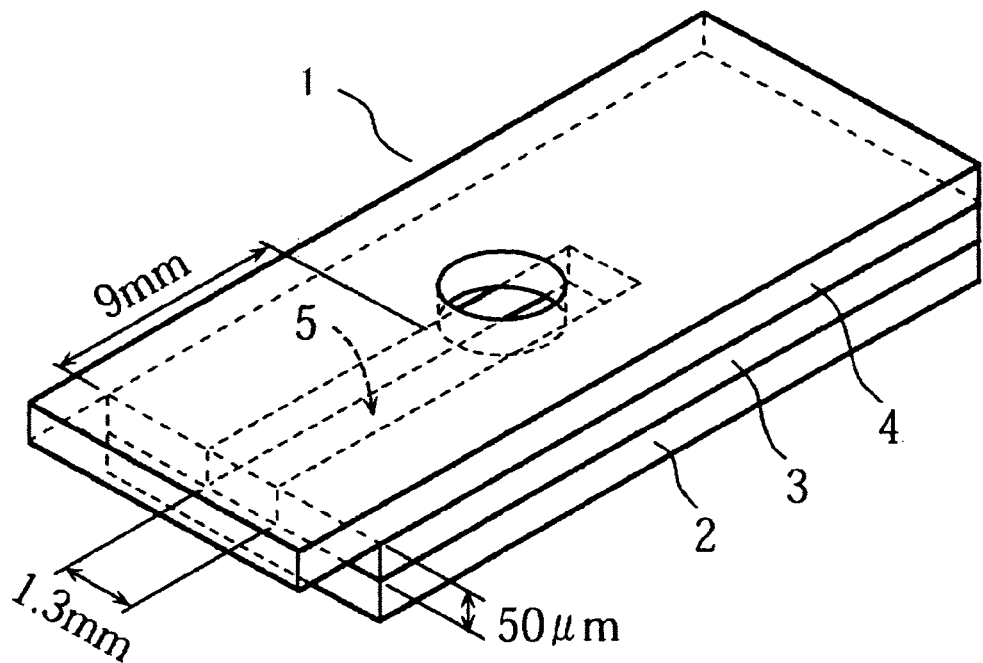
FIG. 9 shows a structure of a glucose sensor.

A glucose sensor (1) having a basic structure shown in FIG. 9 was prepared. That is, the aforementioned glucose sensor had a configuration that a transparent cover (4) (material: PET) was laminated on a transparent base plate (2) via a spacer (3), and the capillary (5) was defined by the elements (2) to (4). The dimension of the capillary (5) was 1.3 mm×9 mm×50 μm (FIG. 9). The transparent base plate (2) and the transparent cover (4) were formed with PET having a thickness of 250 μm, and the spacer (3) was formed with a black double-sided tape.

Figure 10:
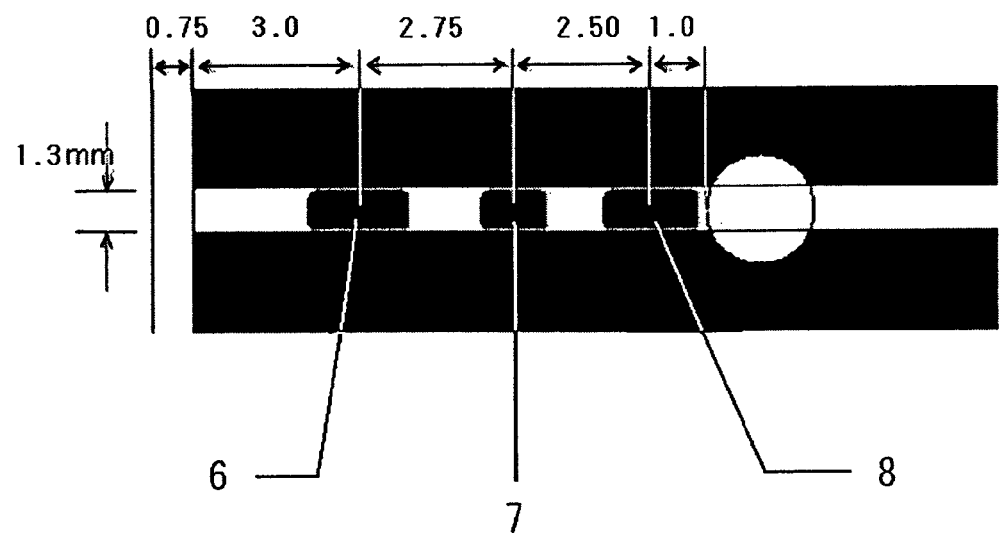
FIG. 10 shows reagent parts of a glucose sensor.

The glucose sensor had a first reagent part (1), a second reagent part (2) and a third reagent part (3) shown in FIG. 10, and ingredients and coating amounts for each part are shown in Table 9. In the table, "Ru" represents a ruthenium hexaammine complex ($Ru(NH_3)_6Cl_3$), CHAPS represents 3-[(3-cholamidopropyl)dimethylammonio]propanesulfonic acid, ACES represents N-(2-acetamido)-2-aminoethanesulfonic acid, and MTT represents 3-(4,5-dimethyl-2-thiazolyl)-2,5-diphenyl-2H-tetrazolium bromide.

TABLE 9

| First reagent part Material solution for reagent part containing electron transfer substance (solvent is water) | |
|---|---|
| Ru | coating |
| 200 mM | 0.2 ul |

| Second reagent part Material solution for reagent part containing enzyme (solvent is water) | | | | |
|---|---|---|---|---|
| enzymes | Enzyme conc. | CHAPS | sucrose monolaurate | ACES (pH 7.5) | coating amount |
| wild type | 15 KU/ml | 0.20% | 0.05% | 75 mM | 0.1 ul |
| 472D475H | 15 KU/ml | 0.20% | 0.05% | 75 mM | 0.1 ul |
| 472E475Y | 15 KU/ml | 0.20% | 0.05% | 75 mM | 0.1 ul |

| Third reagent part Material solution for reagent part containing color developer (solvent is water) | | | |
|---|---|---|---|
| MTT | acrylamide | methanol | coating amount |
| 60 mM | 0.40% | 50% | 0.2 ul |

An assay sample was supplied to the capillary of the aforementioned glucose sensor, and thereafter absorbance was repeatedly measured every 0.1 second to prepare a time course of absorbance. For each measurement of absorbance, the third reagent part (3) was irradiated with light along the direction of the height of the capillary, and light that transmitted through the glucose sensor was received upon the irradiation. The light irradiation was attained by irradiation with light of 630 nm using a light-emitting diode. The transmitted light was received with a photodiode.

Figure 11:
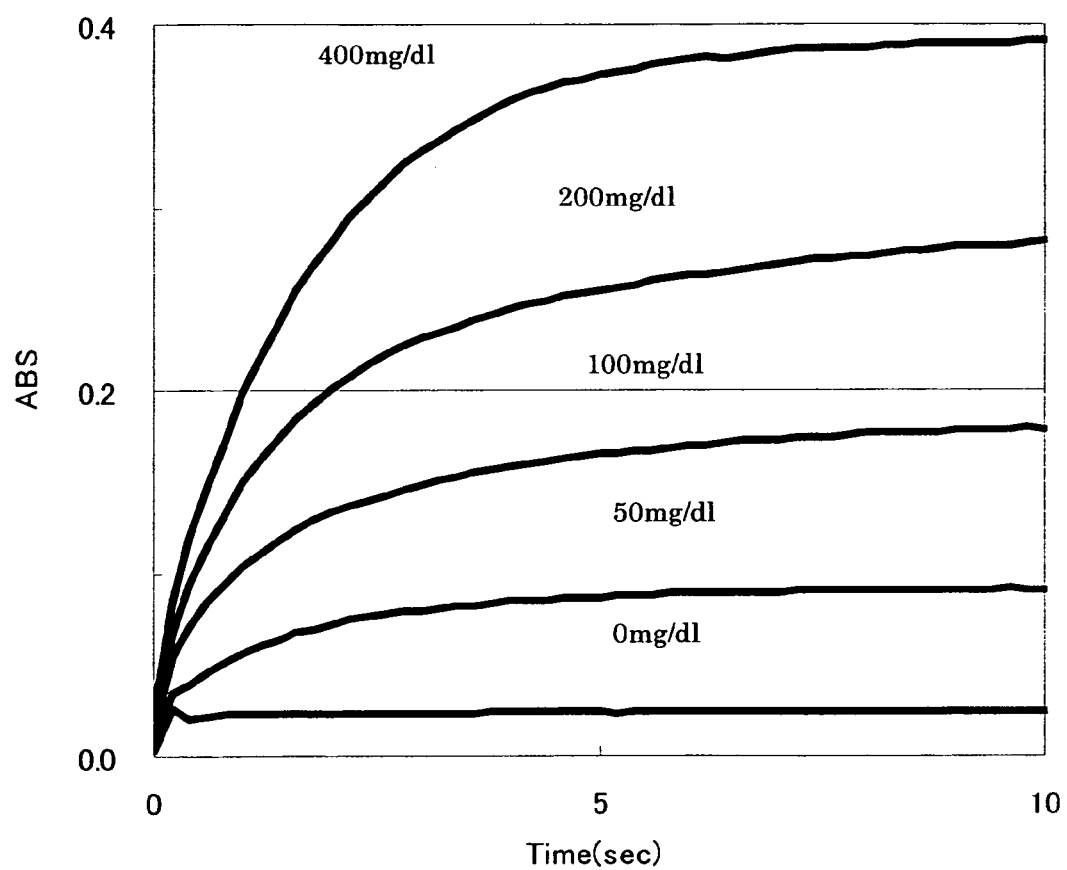
FIG. 11 shows reactivity to glucose of a glucose sensor using a wild type GDH.
Figure 12:
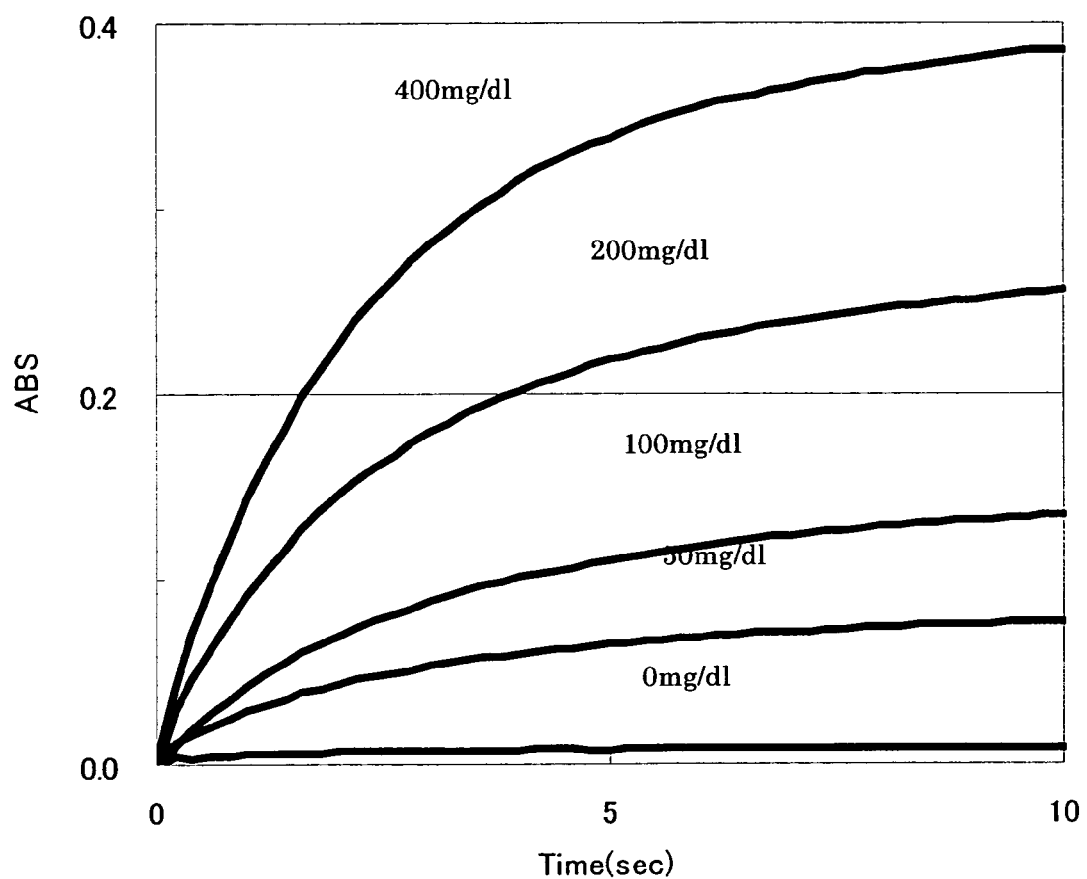
FIG. 12 shows reactivity to glucose of a glucose sensor using 472Glu475Tyr type GDH.
Figure 13:
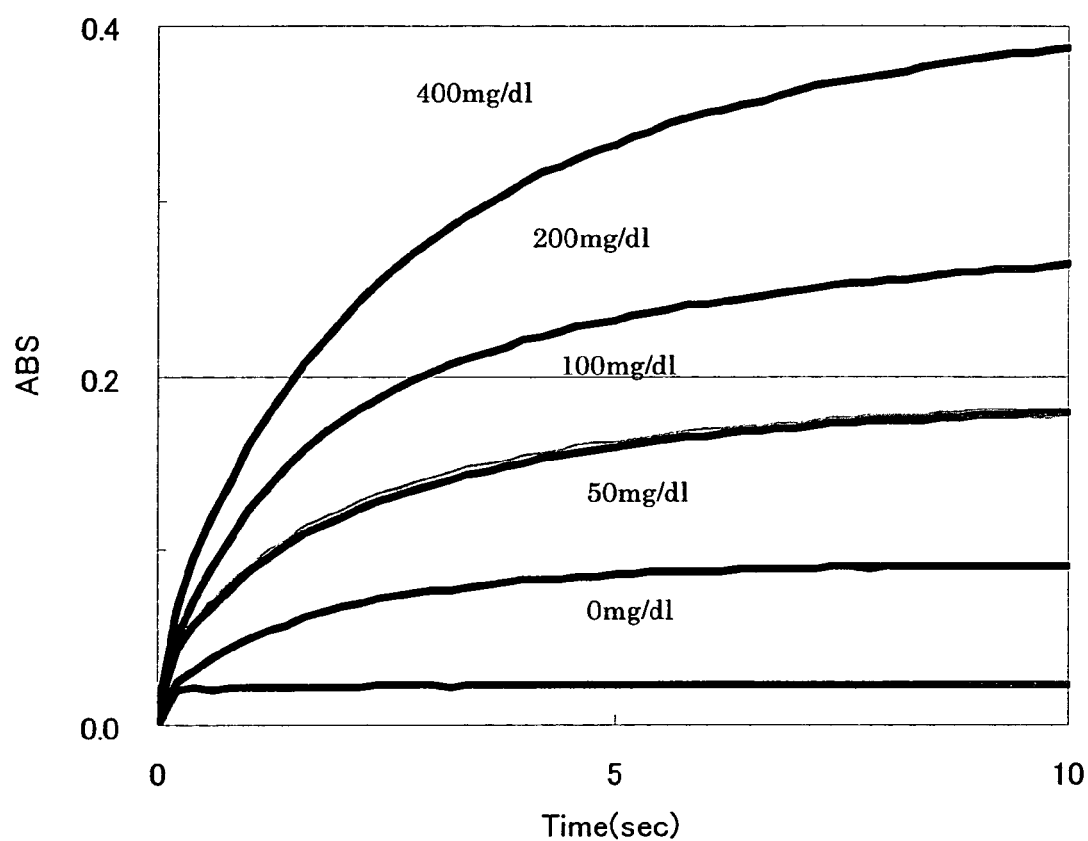
FIG. 13 shows reactivity to glucose of a glucose sensor using 472Asp475His type GDH.

As assay sample, blood added with glucose was used. Blood samples of which hematocrit was adjusted to 42% added with glucose at concentrations of 0, 100, 200 and 400 mg/dl were used to evaluate linearity of the glucose sensor. The results are shown in FIGS. 11 (wild type), 12 (472Glu475Tyr) and 13 (472Asp475His).

Figure 14:
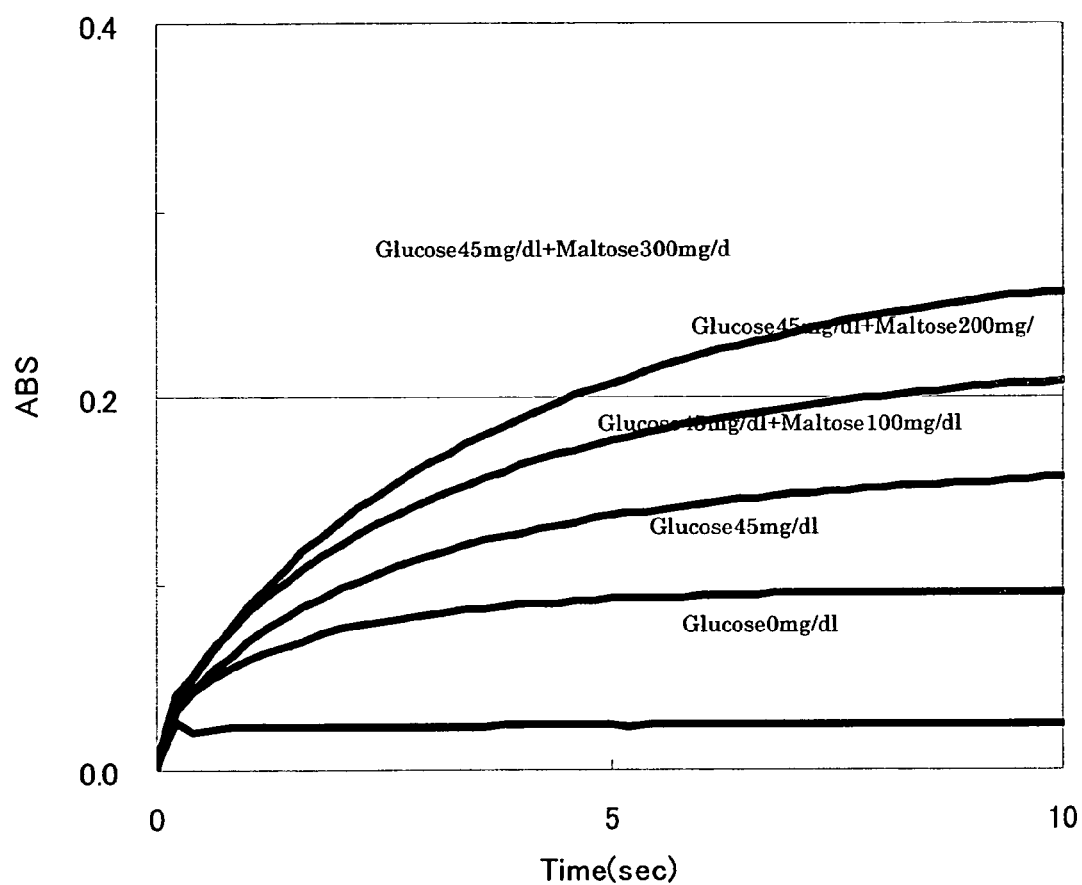
FIG. 14 shows reactivity to maltose of a glucose sensor using a wild type GDH in the presence of glucose.
Figure 15:
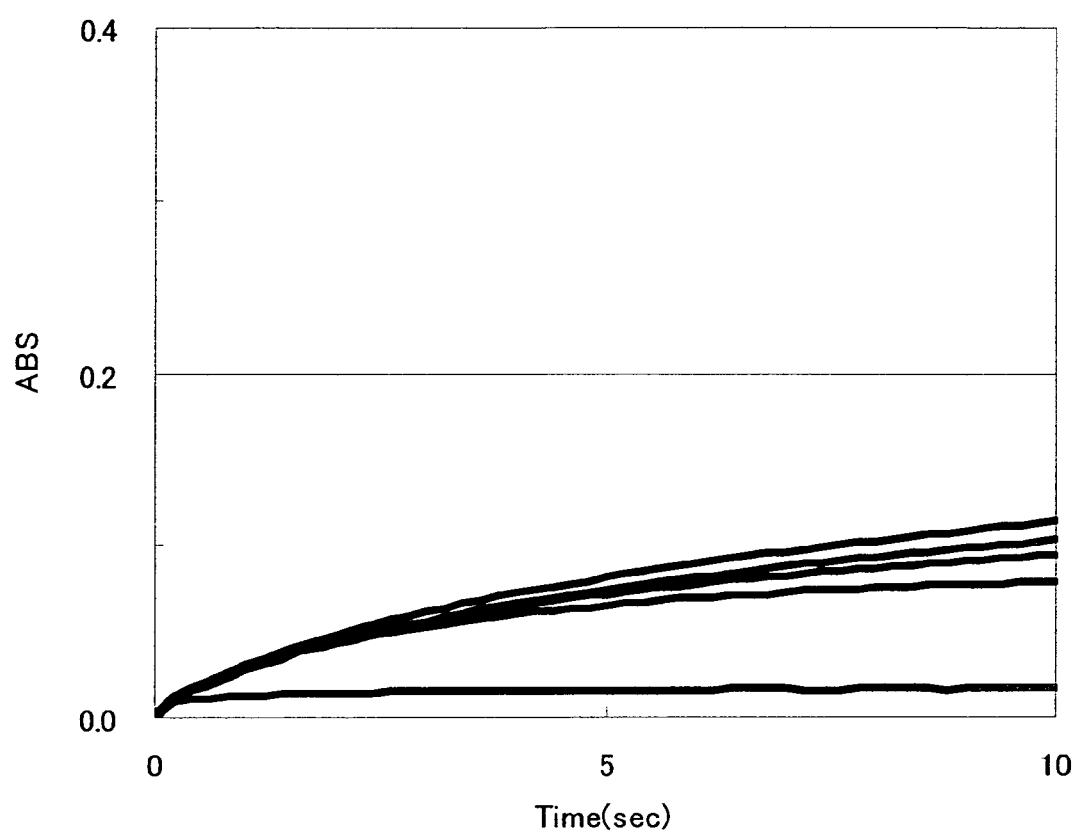
FIG. 15 shows reactivity to maltose of a glucose sensor using 472Glu475Tyr type GDH in the presence of glucose.
Figure 16:
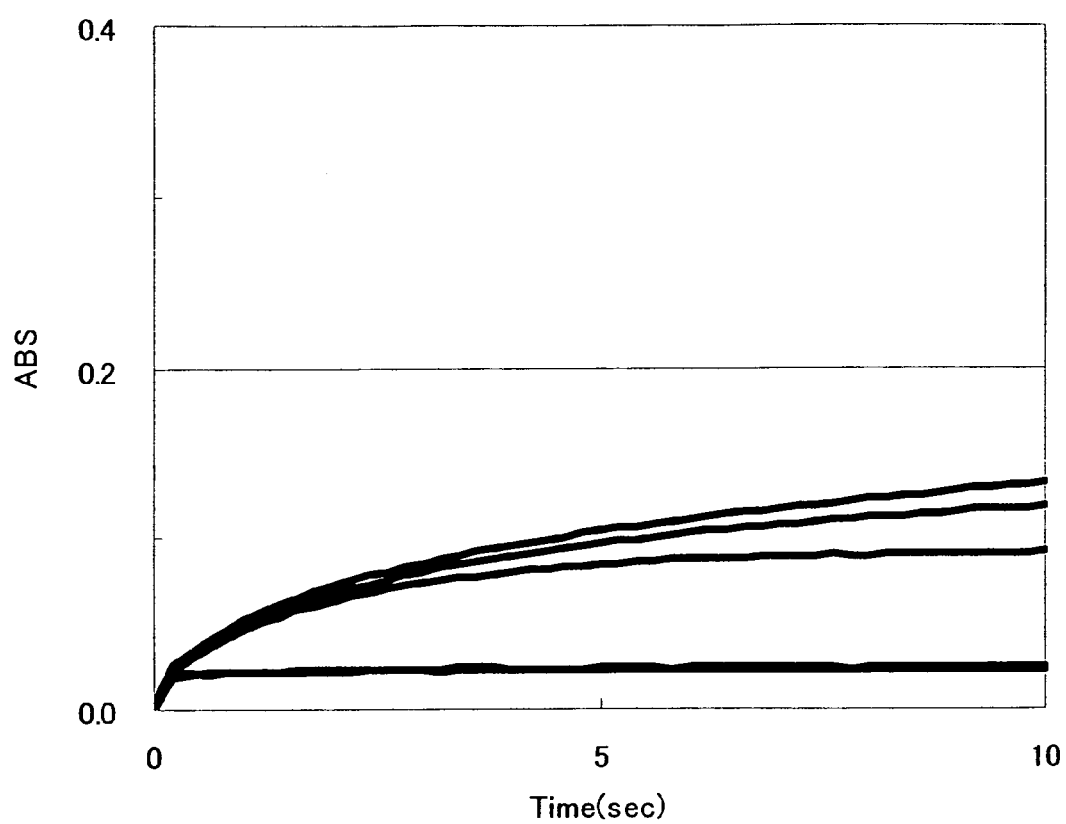
FIG. 16 shows reactivity to maltose of a glucose sensor using 472Asp475His type GDH in the presence of glucose.

Further, blood samples of which hematocrit was adjusted to 42% and glucose concentration was adjusted to 45 mg/dl was further added with maltose at concentrations of 0, 100, 200 and 300 mg/dl, and used to evaluate influence of maltose. The results are shown in FIGS. 14 (wild type), 15 (472Glu475Tyr) and 16 (472Asp475His).

Figure 17:
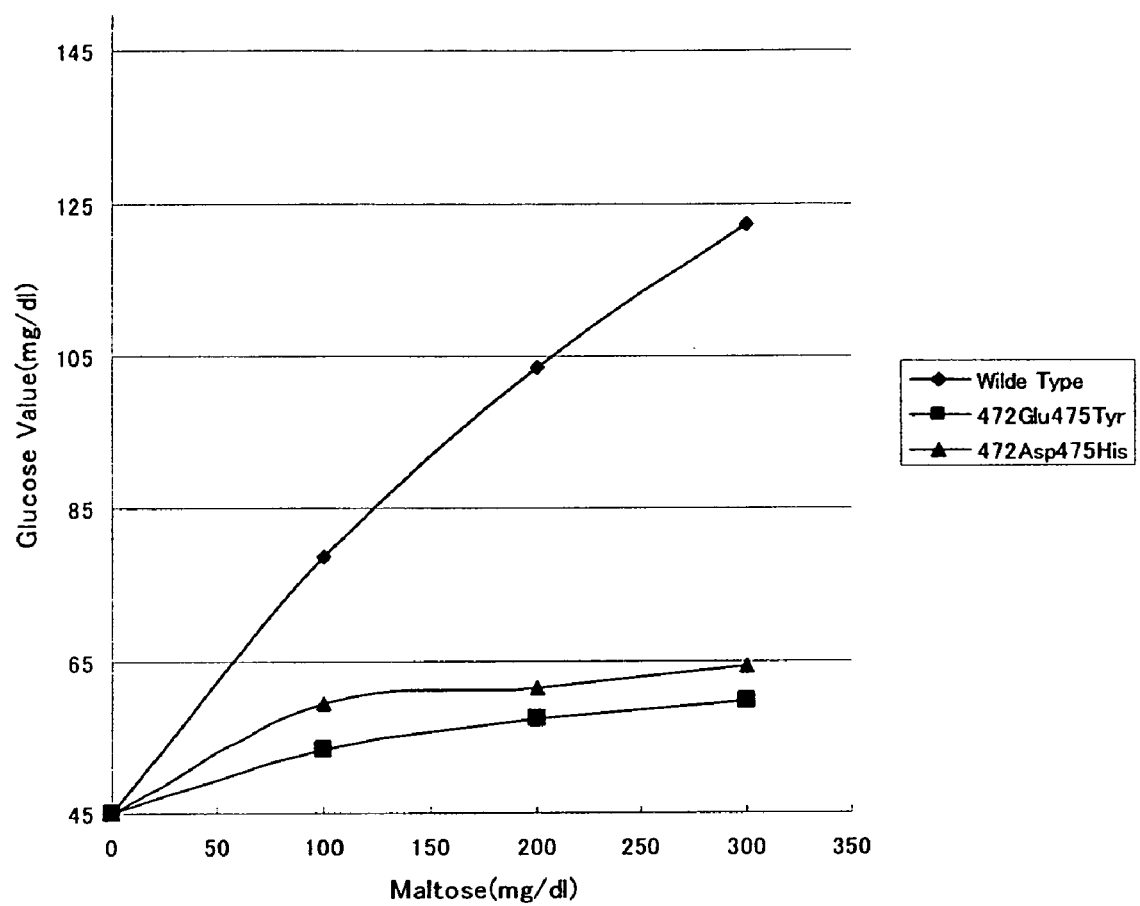
FIG. 17 shows apparent blood sugar levels measured by using glucose sensors using a wild type GDH and a mutant GDH.

When maltose was added to the samples of 45 mg/dl of glucose, absorbance increased in a maltose concentration-dependent manner for the wild type, which suggested strong reaction with maltose. On the other hand, with the sensors using the mutant enzymes, the maltose concentration-dependent increase of the absorbance was suppressed, showing less influence of maltose. The results obtained by converting these data into apparent blood sugar elevation values are shown in FIG. 17. In the sensor using the wild type enzyme, a hypoglycemic level (45 mg/dl of glucose) is apparently shown as a normal value (122 mg/dl of glucose) due to contamination of maltose. On the other hand, when the sensor using the modified GDHs is used, the apparent blood sugar level does not elevate to the normal range even when the sample is contaminated with up to 300 mg/dl of maltose.

As clearly seen from the above results, in the glucose sensors using the mutant GDHs, reactivity to maltose was significantly decreased even though linearity was maintained to an extent comparable to that of the wild type. If these glucose sensors using the mutant GDHs are used, a hypoglycemic value (50 mg/dl or less) is not judged as a normal value or hyperglycemic level even at a maltose blood concentration of the upper limit (200 mg/dl) for administration at hospital or the like or higher, and thus safe therapeutic treatment can be conducted. Further, since GDHs do not react with dissolved oxygen as described above, accurate diagnosis and treatment of diabetic patients can be conducted by providing sensors using these mutant GDHs.

Example 8

Verification of Effect of Combination of Amino Acid Substitution at 472nd Position and Amino Acid Substitution at Position other than 475th Position In a mutant GDH having 472Phe type substitution, substitution of phenylalanine was further introduced at positions in the vicinity of the 475th position (477th to 497th positions) and randomly selected positions far from the 475th position (53rd to 73rd positions).

Mutations were introduced in the same manner as in Example 2 by using pTrc99Aγαβ expressing a mutant GDH containing substitution of phenylalanine at the 472nd position. The sequences of the forward primers used for the introduction of mutations are shown in Tables 10 and 11. The sequences of the reverse primers were completely complementary strands of the forward primers.

TABLE 10

| Mutation | SEQ ID NO: |
|---|---|
| I477F | 19 |
| T478F | 20 |
| G479F | 21 |
| S480F | 22 |
| T481F | 23 |
| I482F | 24 |
| M483F | 25 |
| G484F | 26 |
| A485F | 27 |
| D486F | 28 |
| A487F | 29 |
| R488F | 30 |
| D489F | 31 |
| S490F | 32 |
| V491F | 33 |
| V492F | 34 |
| D493F | 35 |
| K494F | 36 |
| D495F | 37 |
| C496F | 38 |
| R497F | 39 |

TABLE 11

| Mutation | SEQ ID NO: |
|---|---|
| R53F | 40 |
| N54F | 41 |
| Q55F | 42 |
| P56F | 43 |
| D57F | 44 |
| K58F | 45 |
| M59F | 46 |
| D60F | 47 |
| M62F | 48 |
| A63F | 49 |
| P64F | 50 |
| Y65F | 51 |
| P66F | 52 |
| S67F | 53 |
| S68F | 54 |
| P69F | 55 |
| W70F | 56 |
| A71F | 57 |
| P72F | 58 |
| H73F | 59 |

The results are shown in Tables 12 and 13. As clearly seen from these results, with combinations of amino acid substitution of 472Phe and substitution at positions other than the 475th position, activity was lost, no change occurred, or only an effect of increasing the reactivity to maltose was observed, and thus it was confirmed that the improving effect was not necessarily obtained by introducing mutations at any arbitrary positions.

TABLE 12

| | mutated site | substituting amino acid | 10 mM Glucose U/ml | 10 mM Maltose U/ml | Mal/Glu reaction ratio |
|---|---|---|---|---|---|
| 472F | | None | 6.79 | 0.81 | 12% |
| 472F+ | 475 | F(Phe) | 0.75 | 0.07 | 8.7% |
| 472F+ | 477 | F(Phe) | 0.11 | 0.16 | inactive |
| 472F+ | 478 | F(Phe) | 0.12 | 0.12 | inactive |
| 472F+ | 479 | F(Phe) | 0.21 | 0.21 | inactive |
| 472F+ | 480 | F(Phe) | 0.26 | 0.30 | inactive |
| 472F+ | 481 | F(Phe) | 0.10 | 0.08 | inactive |
| 472F+ | 482 | F(Phe) | 0.06 | 0.08 | inactive |
| 472F+ | 483 | F(Phe) | 4.32 | 0.68 | 15.6% |

TABLE 12-continued

| mutated site | substituting amino acid | 10 mM Glucose U/ml | 10 mM Maltose U/ml | Mal/Glu reaction ratio |
|---|---|---|---|---|
| 472F+ | 484 F(Phe) | 0.10 | 0.10 | inactive |
| 472F+ | 485 F(Phe) | 0.18 | 0.24 | inactive |
| 472F+ | 486 F(Phe) | 1.26 | 0.40 | 32.0% |
| 472F+ | 487 F(Phe) | 0.22 | 0.23 | inactive |
| 472F+ | 488 F(Phe) | 2.85 | 0.65 | 22.9% |
| 472F+ | 489 F(Phe) | 1.81 | 0.56 | 31.2% |
| 472F+ | 490 F(Phe) | 0.18 | 0.19 | inactive |
| 472F+ | 491 F(Phe) | 0.23 | 0.23 | inactive |
| 472F+ | 492 F(Phe) | 0.19 | 0.24 | inactive |
| 472F+ | 493 F(Phe) | 0.15 | 0.15 | inactive |
| 472F+ | 494 F(Phe) | 1.15 | 0.29 | 25.0% |
| 472F+ | 495 F(Phe) | 0.29 | 0.23 | inactive |
| 472F+ | 496 F(Phe) | 0.16 | 0.18 | inactive |
| 472F+ | 497 F(Phe) | 0.14 | 0.16 | inactive |

TABLE 13

| mutated site | substituting amino acid | 10 mM Glucose U/ml | 10 mM Maltose U/ml | Mal/Glu reaction ratio |
|---|---|---|---|---|
| 472F | None | 6.79 | 0.81 | 11.9% |
| 472F+ | 475 F(Phe) | 0.75 | 0.07 | 8.7% |
| 472F+ | 53 F(Phe) | 3.44 | 0.48 | 13.8% |
| 472F+ | 54 F(Phe) | 3.00 | 0.54 | 18.2% |
| 472F+ | 55 F(Phe) | 3.81 | 0.72 | 18.8% |
| 472F+ | 56 F(Phe) | 4.89 | 0.57 | 11.7% |
| 472F+ | 57 F(Phe) | 2.41 | 0.41 | 17.2% |
| 472F+ | 58 F(Phe) | 3.33 | 0.45 | 13.5% |
| 472F+ | 59 F(Phe) | 4.07 | 0.58 | 14.2% |
| 472F+ | 60 F(Phe) | 1.55 | 0.37 | 23.7% |
| 472F+ | 62 F(Phe) | 1.31 | 0.26 | 19.9% |
| 472F+ | 63 F(Phe) | 2.91 | 0.44 | 15.0% |
| 472F+ | 64 F(Phe) | 0.54 | 0.28 | 51.4% |
| 472F+ | 65 F(Phe) | 5.52 | 0.76 | 13.8% |
| 472F+ | 66 F(Phe) | 1.63 | 0.35 | 21.8% |
| 472F+ | 67 F(Phe) | 3.91 | 0.48 | 12.3% |
| 472F+ | 68 F(Phe) | 4.32 | 0.86 | 19.8% |
| 472F+ | 69 F(Phe) | 4.79 | 0.82 | 17.1% |
| 472F+ | 70 F(Phe) | 5.34 | 0.64 | 12.0% |
| 472F+ | 71 F(Phe) | 1.26 | 0.28 | 22.5% |
| 472F+ | 72 F(Phe) | 3.65 | 0.50 | 13.8% |
| 472F+ | 73 F(Phe) | 1.20 | 0.26 | 21.3% |

INDUSTRIAL APPLICABILITY

The mutant GDH of the present invention has improved substrate specificity to glucose and can be suitably used for measurement of glucose using a glucose sensor or the like.

What is claimed is:

1. An isolated mutant glucose dehydrogenase exhibiting improved substrate specificity to glucose, which is
   (1) a mutant of the protein comprising the amino acid sequence of SEQ ID NO: 13, wherein said mutant consists of amino acid substitution(s) at positions 472 and/or 475 as listed below in (A)-(C); or
   (2) a mutant of the protein comprising the amino acid sequence of SEQ ID NO: 13 wherein said mutant consists of amino acid substitution(s) at positions 472 and/or 475 as listed below in (A)-(C) and consists of substitution, deletion, insertion or addition of one to ten amino acid residues at position(s) other than the positions listed below and wherein mutants (1) or (2) have glucose dehydrogenase activity (numerals represent a position in the amino acid sequence, the amino acid residues represent an amino acid residue after substitution at the position, and "+" means that two amino acid substitutions are simultaneously included), wherein improved substrate specificity for mutants (1) or (2) is a decrease of at least 10% in the ratio of reactivity to maltose/reactivity to glucose compared to the glucose dehydrogenase of SEQ ID NO: 13:
   (A) 472Arg, 472Asn, 472Asp, 472Cys, 472Glu, 472Gly, 472His, 472Ile, 472Leu, 472Met, 472Phe, 472Pro, 472Ser, 472Trp, 472Tyr, or 472Val;
   (B) 475Asp, 475Cys, 475Glu, 475Gly, 475His, 475Met, 475Phe, 475Ser, 475Tyr, or 475Val; or
   (C) 472Arg +475(Asp, Glu, Gly, His, Phe, Ser, Tyr),
   472Asn +475(Asp, Gly, His, Phe, Ser, Tyr),
   472Asp +475(His, Phe, Ser, Val),
   472Cys +475(Asp, Gly, His, Phe, Ser),
   472Glu +475(Asp, Glu, Gly, His, Phe, Ser, Tyr),
   472Gly +475(Asp, Cys, Gly, Met, Phe, Ser, Tyr),
   472His +475(Cys, Glu, His, Met, Phe, Ser, Tyr),
   472Ile +475(Asp, Cys, Glu, Gly, His, Met, Phe, Ser, Tyr),
   472Leu +475(Asp, Gly, His, Phe, Ser, Tyr),
   472Met +475(Asp, Gly, His, Phe, Ser),
   472Phe +475(Asp, Glu, Gly, His, Met, Phe, Ser, Tyr),
   472Pro +475His
   472Ser +475(Asp, Glu, Gly, His, Phe, Ser),
   472Trp +475(His, Phe, Ser),
   472Tyr +475(Asp, His, Phe, Ser), or
   472Val +475(Asp, Glu, Gly, His, Phe, Ser).

2. The isolated mutant glucose dehydrogenase according to claim 1, which consists of amino acid substitution(s) at positions 472 and/or 475 selected from (A) to (C).

3. The isolated mutant glucose dehydrogenase according to claim 1, wherein the substitutions at positions 472 and/or 475 consist of the amino acid substitution(s) listed in (D) to (F):
   (D) 472Arg, 472Asn, 472Asp, 472Glu, 472Gly, 472Phe, or 472Pro,
   (E) 475Asp, 475Cys, 475Glu, 475Gly, 475Met, or 475Phe, or
   (F) 472Arg +475(Asp, Gly, His, Phe),
   472Asn +475(Gly, His, Phe, Tyr),
   472Asp +475(His, Ser),
   472Cys +475(Gly, His, Phe),
   472Glu +475(Glu, His, Phe, Tyr),
   472Gly +475(Asp, Phe, Tyr),
   472His +475(His, Ser),
   472Ile +475(Asp, Glu, Gly, His, Ser),
   472Leu +475(Gly, His, Phe, Tyr),
   472Met +475(Asp, Gly, His, Phe),
   472Phe +475(Asp, Glu, Gly, His, Phe, Ser, Tyr),
   472Ser +475(Glu, Gly, His, Phe),
   472Trp +475(His, Phe),
   472Tyr +475His, or
   472Val +475(Asp, Glu, Gly, His, Phe).

4. An isolated glucose dehydrogenase, which is
   (1) a mutant of the protein comprising the amino acid sequence of SEQ ID NO: 13, wherein said mutant consists of amino acid substitution(s) at positions 472 and/or 475, or
   (2) a mutant of the protein comprising the amino acid sequence of SEQ ID NO: 13, wherein said mutant consists of amino acid substitution(s) at positions 472 and/or 475 and consists of substitution, deletion, insertion or addition of one to ten amino acid residues at position other than positions 472 and/or 475, wherein mutants 1 or 2 have a glucose dehydrogenase activity, and wherein:
   (i) the substitutions at positions 472 and/or 475 in mutants (1) or (2) consist of replacement of at least either the arginine residue at position 472 or the asparagine residue at position 475 in the amino acid sequence of SEQ ID NO: 13 with another amino acid residue, and
   (ii) a ratio of specific activity for glucose and specific activity for maltose ((reactivity to maltose/reactivity to glucose)×100) of the glucose dehydrogenase of mutants (1) or (2) is reduced by 10% or more compared with that of the glucose dehydrogenase of SEQ ID NO: 13.

5. A mutant glucose dehydrogenase complex comprising at least the isolated mutant glucose dehydrogenase according to claim 1 and an electron transfer subunit.

6. A glucose assay kit comprising the mutant glucose dehydrogenase according to claim 1, optionally in combination with an electron transfer subunit.

7. A glucose sensor comprising the mutant glucose dehydrogenase according to claim 1, optionally in combination with an electron transfer subunit.

8. A mutant glucose dehydrogenase complex comprising at least the isolated mutant glucose dehydrogenase according to claim 4 and an electron transfer subunit.

9. A glucose assay kit comprising the mutant glucose dehydrogenase according to claim 4, optionally in combination with an electron transfer subunit.

10. A glucose sensor comprising the mutant glucose dehydrogenase according to claim 4, optionally in combination with an electron transfer subunit.

11. A mutant glucose dehydrogenase complex comprising at least the isolated mutant glucose dehydrogenase according to claim 2 and an electron transfer subunit.

12. A glucose assay kit or glucose sensor comprising the mutant glucose dehydrogenase according to claim 2, optionally in combination with an electron transfer subunit.

13. A mutant glucose dehydrogenase complex comprising at least the isolated mutant glucose dehydrogenase according to claim 3 and an electron transfer subunit.

14. A glucose assay kit or glucose sensor comprising the mutant glucose dehydrogenase according to claim 3, optionally in combination with an electron transfer subunit.

* * * * *